United States Patent
Tangy et al.

(10) Patent No.: US 11,020,473 B2
(45) Date of Patent: Jun. 1, 2021

(54) COMPOSITIONS AND METHODS COMPRISING MEASLES VIRUS DEFECTIVE INTERFERING PARTICLES FOR THE PREVENTION OF INFECTIOUS DISEASES

(71) Applicants: INSTITUT PASTEUR, Paris (FR); CENTRE NATIONAL DE LA RECHERCHE SCIENTIFIQUE, Paris (FR); MINISTÈRE DES ARMÉES—Direction Centrale du Service de Santé des Armées, Paris (FR)

(72) Inventors: Frederic Tangy, Les Lilas (FR); Anastassia Komarova, Arcueil (FR); Marie Mura, Avrainville (FR); Chantal Combredet, Paris (FR)

(73) Assignees: INSTITUT PASTEUR, Paris (FR); CENTRE NATIONAL DE LA RECHERCHE SCIENTIFIQUE, Paris (FR); MINISTÈRE DES ARMÉES—Direction Centrale du Service de Sante des Armée, Paris (FR)

( * ) Notice: Subject to any disclaimer, the term of this patent is extended or adjusted under 35 U.S.C. 154(b) by 0 days.

(21) Appl. No.: 16/311,457

(22) PCT Filed: Jun. 23, 2017

(86) PCT No.: PCT/IB2017/000965
§ 371 (c)(1),
(2) Date: Dec. 19, 2018

(87) PCT Pub. No.: WO2017/221076
PCT Pub. Date: Dec. 28, 2017

(65) Prior Publication Data
US 2019/0184003 A1 Jun. 20, 2019

Related U.S. Application Data

(60) Provisional application No. 62/354,363, filed on Jun. 24, 2016.

(51) Int. Cl.
| | |
|---|---|
| *A61K 39/165* | (2006.01) |
| *A61K 39/12* | (2006.01) |
| *A61K 39/295* | (2006.01) |
| *A61K 39/015* | (2006.01) |
| *A61K 39/39* | (2006.01) |
| *A61P 33/00* | (2006.01) |
| *A61P 31/00* | (2006.01) |
| *A61K 39/00* | (2006.01) |

(52) U.S. Cl.
CPC ............ *A61K 39/12* (2013.01); *A61K 39/015* (2013.01); *A61K 39/39* (2013.01); *A61P 31/00* (2018.01); *A61P 33/00* (2018.01); *A61K 2039/51* (2013.01); *A61K 2039/5254* (2013.01); *A61K 2039/5256* (2013.01); *A61K 2039/5258* (2013.01); *A61K 2039/545* (2013.01); *A61K 2039/555* (2013.01); *A61K 2039/55588* (2013.01); *A61K 2039/70* (2013.01); *C12N 2740/16134* (2013.01); *C12N 2740/16234* (2013.01); *C12N 2760/18434* (2013.01); *C12N 2760/18443* (2013.01); *C12N 2760/18444* (2013.01); *C12N 2770/36134* (2013.01); *Y02A 50/30* (2018.01)

(58) Field of Classification Search
CPC ........ A61K 38/00; A61K 39/00; A61K 39/12; A61K 39/165
USPC .......... 424/184.1, 199.1, 201.1, 204.1, 212.1
See application file for complete search history.

(56) References Cited

FOREIGN PATENT DOCUMENTS

| WO | 2004001051 A2 | 12/2003 |
|---|---|---|
| WO | 2008065752 A1 | 6/2008 |
| WO | 2014049094 A1 | 4/2014 |
| WO | 2016198642 A1 | 12/2016 |

OTHER PUBLICATIONS

International Search Report and Written Opinion for PCT/IB2017/000965 dated Oct. 9, 2017 (16 pages).
Shivakoti et al., "Induction of Dendritic Cell Production of Type I and Type III Interferons by Wild-Type and Vaccine Strains of Measles Virus: Role of Defective Interfering RNA's," Journal of Virology, 87(14):7816-7827 (2013).

*Primary Examiner* — Rodney P Swartz
(74) *Attorney, Agent, or Firm* — Arrigo, Lee, Guttman & Mouta-Bellum LLP

(57) ABSTRACT

The invention is in the field of prevention or treatment of diseases, in particular infectious diseases, and more particularly in the field of multivalent vaccines. The inventors characterized 5' copy-back DI-RNAs produced by recombinant MV strains, including rMV-based vaccines and wild-type MV (wt-MV). The efficiency of these DI-RNAs productions in different cell types was compared. For the first time 5' copy-back DI-RNAs specific binding to RIG-I, MDA5 and LGP2 was assessed and linked to functional outcome in type-I IFN signalling. The inventors provide a composition of products comprising at least (i) a mixture of particles of a rescued recombinant MV-derived virus encoding at least one antigen (ii) a recombinant and/or purified protein, comprising at least one antigen. Regardless of the presentation of the products, and in particular regardless of whether the products are separated or readily separable or presented as a mixture.

Figure 1A:
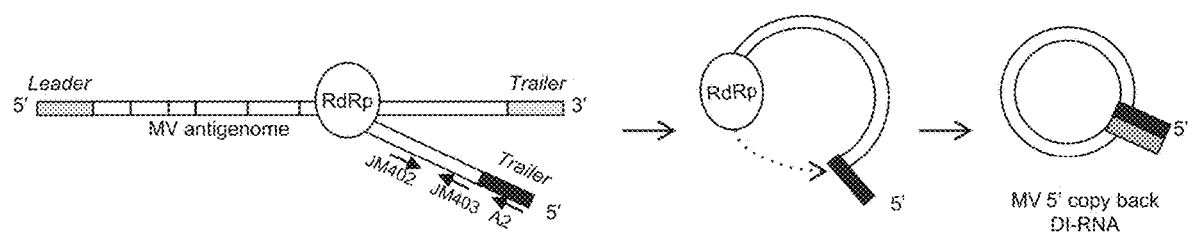

19 Claims, 11 Drawing Sheets
Specification includes a Sequence Listing.

COMPOSITIONS AND METHODS COMPRISING MEASLES VIRUS DEFECTIVE INTERFERING PARTICLES FOR THE PREVENTION OF INFECTIOUS DISEASES

FIELD OF THE INVENTION

The invention is in the field of prevention or treatment of diseases, in particular infectious diseases, and more particularly in the field of multivalent vaccines.

BACKGROUND

Defective interfering (DI) genomes are produced by most viruses. They are truncated forms of the viral genome that are generated during virus replication. DI and viral genomes share the minimum essential characteristics for replication: a competent initiation site at 3' termini, the complement of an initiation site at 5' termini and structure or sequence that is required for encapsidation into a nucleocapsid (1). However, DI genomes are defective for replication in the absence of the complete functional virus genome to provide the missing functions. DI genomes, and more precisely the 5'copy-back DI genome or DI-RNA is well described for paramyxoviruses. This specific type of DI genomes are produced when the viral polymerase, due to yet unknown mechanism, detaches from the template and reattaches to the newly synthesizing strand, copying back the 5' end of the genome.

Paramyxoviruses, as other members of order Mononegavirales, possess linear, non-segmented negative-sense, single-stranded RNA genomes, with virus replication set in the cytoplasm. The RNA genome of Paramyxoviridae encodes six structural proteins. While hemagglutinin (H) and fusion (F) are transmembrane glycoproteins, the nucleoprotein (N), the phosphoprotein (P) and the viral RNA-dependent RNA polymerase (RdRp, or L) assemble into ribonucleoprotein complexes (RNPs) that ensure viral genome transcription and replication in the cytoplasm of infected cells. Replication of these viruses is coupled to encapsidation so that full-length antigenomes and genomes are found only inside assembled nucleocapsids (4). Matrix protein (M) recruit assembled RNPs underneath the cellular membrane, and participate to the budding of viral particles underlies the lipid bilayer where it interacts with the nucleocapsid. In addition to the structural proteins, the P gene of paramyxoviruses encodes nonstructural, genus-specific, virulence factors. For measles virus (MV) these are the C and V proteins whose expression is achieved by site-specific editing of the P mRNA by the viral RdRp to produce V, or by the use of overlapping open reading frames to produce C.

5' copy-back DI-RNAs of paramyxoviruses are able to induce type-I interferon (IFN-(3) signalling, due to their structural characteristics: a double stranded stem with perfectly complementary ends and a 5' triphosphate extremity (7-8). These RNA molecules activate innate signalling through cytosolic RIG-I-like receptors (RLRs). Indeed, 5' copy-back DI genomes have been described as pathogen-associated molecular patterns (PAMPs) for RIG-I (11-13) and MDA5 (12). Whether LGP2, which is the third known RLR, can also specifically interact with 5' copy-back DI genomes is not known. Furthermore, RIG-I-dependent IFN-β signalling mediated by 5'copy-back DI genome is enhanced in the presence of Interferon-inducible double-stranded RNA-dependent protein kinase activator A (PACT) that also binds the DI RNA. Additionally, accumulation of DI-RNAs is the trigger for double-stranded RNA-dependent protein kinase (PKR) activation that generates a cellular stress response, resulting in translational arrest and formation of stress granules.

DI genomes have been identified in human infections with influenza virus, dengue virus, Hepatitis C virus and more recently with a paramyxovirus, respiratory syncytial virus (RSV). Interestingly the rate of accumulation of DI genomes during infection with RSV had a direct correlation with the quality of the antiviral response. Indeed, early accumulation of DI genomes was a good prognostic for viral clearance and full disease recovery (19). For MV, 5' copy-back DI genomes were not found in vivo during natural infection (20), nor after MV vaccination (no data available). It is well known that viral stocks of standard live attenuated vaccines are variable producers of DI genomes (8,20). Attenuated MV Schwarz strain that is routinely used in our laboratory is a poor producer of DI genomes. In cell cultures, production of DI-RNAs is depending on the multiplicity of infection (MOI) and the number of cell passages. However, several modifications of MV genome lead to efficient DI-RNA production by modified strains: recombinant MV (rMV) expressing an additional copy of MV-N (rMV-N) (10), rMV-ΔC and rMV-ΔV lacking the expression of two virulent proteins, respectively C and V proteins (13,23).

MV is a promising vaccine vector to deliver heterologous antigen. Indeed, a recent Phase I trial of a rMV-chikungunya vaccine has demonstrated that the human pre-immunity against MV does not interfere with acquisition of immunity against the heterologous pathogen (24). If in comparison to the backbone MV-Schwarz strain rMV-based vaccines are also efficient producers of DI-RNAs, this would suggest an additional intrinsic immunostimulatory activity for rMV-based vaccines.

DESCRIPTION OF THE INVENTION

The inventors characterized 5' copy-back DI-RNAs produced by recombinant MV strains, including rMV-based vaccines and wild-type MV (wt-MV). The efficiency of these DI-RNAs productions in different cell types was compared. For the first time 5' copy-back DI-RNAs specific binding to RIG-I, MDA5 and LGP2 was assessed and linked to functional outcome in type-I IFN signalling.

The inventors provide a composition of products comprising at least (i) a mixture of particles of a rescued recombinant MV-derived virus encoding at least one antigen (ii) a recombinant and/or purified protein, comprising at least one antigen. Regardless of the presentation of the products, and in particular regardless of whether the products are separated or readily separable or presented as a mixture, the composition is herein designated composition of products of the invention. Accordingly, the composition of products of the invention encompasses products presented as a single mixture or as an assembly of physically separated products, also designated as a kit of products.

The particles of the rescued recombinant MV-derived virus comprise both infectious replicating viral particles, i.e. viral particles that can replicate in host cells independently of the presence of other particles, in particular viral particles comprising the whole genome of the MV-derived virus, and DI particles, i.e. particles comprising a portion of the genome of the MV-derived virus, which may only replicate in host cells if said cells also comprise replicating viral particles. In a particular embodiment, the particles of the rescued recombinant MV-derived virus comprise infectious replicating viral particles, DI particles and also DI RNA. In particular embodiments, the DI genomes represent at least 0.00001% of the full-length MV genomic RNA in the composition, preferably at least 0.001%, more preferably at least 0.1% and even more preferably at least 1% or 10% of the full-length MV genomic RNA in the composition. % of RNA is intended to mean % in molar content as detected by qRT-PCR. In particular embodiments, the DI genomes are produced by cells producing MV-derived infectious viral particles and in particular are encapsidated into the nucleocapsid of MV. DI particles designate DI genomes encapsidated into nucleocapsids, while the DI genome designates both naked DI RNA (such as in vitro transcribed DI RNA) and encapsidated RNA. The mixture of particles is designated herein "the MV-derived particles".

The DI genomes being incomplete, when referring herein to features of the genome of the MV-derived particles, said features are disclosed in regard of the whole genome, and apply to the DI genomes only inasmuch as the corresponding portion of the whole genome is comprised in the DI genomes. In particular, for example, when it is stated herein that the MV-derived particles encode an antigen, it must be understood that the genome of the corresponding MV-derived virus encodes said antigen, while the DI genomes produced by cells producing said virus do not usually comprise the coding sequence for the antigen.

The antigen or antigens encoded by the MV-derived viral particles are designated herein the "vectored antigen" or "vectored antigens". The antigen or antigens provided as proteins (synthesized, recombinant and/or purified) in the composition of products of the invention are designated herein the "protein antigen" or "protein antigens". Singular or plural forms are used interchangeably and the use of either does not, unless explicitly provided, limit the disclosure to a single vectored antigen or several vectored antigens or to a single protein antigen or several protein antigens. The skilled person will indeed realize that the invention may be used indifferently with one or several vectored antigens and with one or several protein antigens. For the sake of clarity, it is specified that the expression vectored antigen refers to the antigen itself, and not to the vector comprising the antigen; depending on the context, as the skilled person will readily understand, the expression primarily refers to the antigen as a polypeptide but may also refer, where relevant, to the polynucleotide encoding said antigen.

As used herein, a protein designates a polypeptide of any size, in particular a polypeptide of at least 4 amino acids, preferably at least 6 amino acids. In particular embodiments, the vectored antigen is a polypeptide of a size from 6 to 1000 amino acids, in particular from 6 to 500 amino acids, more particularly from 6 to 300 amino acids, from 6 to 100 or from 6 to 50 amino acids. In particular embodiments, the protein antigen is a polypeptide of a size from 6 to 1000 amino acids, in particular from 6 to 500 amino acids, from 20 to 1000 amino acids, from 50 to 1000 amino acids, from 20 to 500 or from 50 to 500 amino acids.

As the skilled person is aware, the composition of products of the invention is similar in structure, features and use whether the antigen provided in the composition as a protein is obtained by chemical synthesis, produced as a recombinant protein in an in vitro cellular or cell-free production system, or purified from a biological sample naturally containing said protein. In most applications, the use of a recombinant protein is expected to be the most advantageous in terms of safety and cost. The expression "protein antigen" is used herein to designate the antigen which is provided (or the antigens which are provided) in the composition as a protein (or as proteins), and is not intended to limit the disclosure to recombinant proteins. The protein may be provided in any suitable form and in particular it may be advantageous to provide the protein antigen as virus-like particles. In any of the embodiments, the composition of products of the invention may comprise VLPs and/or the protein antigen is provided as part of a VLP.

In particular embodiments, the MV-derived viral particles of the composition of products of the invention encode at least one antigen which is not from MV. In particular embodiments, the vectored antigen and the protein antigen are from the same infectious species. In particular embodiments, the vectored antigen and the protein antigen are from at least two distinct infectious species, in particular from two distinct viruses. In particular embodiments, the MV-derived viral particle encodes at least two distinct antigens. In particular embodiments, the composition of products of the invention comprises at least two distinct protein antigens.

In particular embodiments, the vectored antigen and the protein antigen are the same antigen. In particular, the protein antigen may be a recombinant protein encoded by the nucleic acid sequence encoding the vectored antigen. In particular embodiments, at least one of the vectored antigens is the same as at least one of the protein antigens.

In particular embodiments, at least one antigen is from an arbovirus. In particular embodiments, the arbovirus is selected from the group consisting of alphavirus: Chikungunya Virus (CHIKV) and equine encephalitis virus (VVEV, EEV, WEEV), flavivirus:Dengue Virus (DV), West-Nile Virus (WNV), Yellow Fever Virus (YFV) and, ZIKA virus (ZV)

In particular embodiments, the antigen from CHIKV comprises structural proteins of the Chikungunya virus, in particular one or several CHIKV structural proteins E1, E2, E3, C and 6K and/or the E3-E2-6K-E1 polyprotein and more particularly the antigens described in (28). In particular, the antigen from CHIKV is a soluble form of the envelope protein E2, optionally without the stem region, the ectodomain of the envelope protein E2. In particular embodiments, the CHIKV is as described in WO 2014049094 A1, in particular is encoded by a nucleic acid having the sequence numbered as 3, 5, 7, 9, 30, 11, 13, 15, 17, 19, 21, 22, 23, 24, 25, 26 or 28 in the sequence listing of said publication.

In particular embodiments, the antigen from DV is the M protein, or the E protein, or a fraction thereof, and/or is as disclosed in WO2015/197565 A1, in particular said antigen is a chimeric polyepitope having less than 600 amino acid residues comprising or consisting of the following fragments of (a), (b) and (c) assembled in a fusion polypeptide wherein the fragments of (a), (b) and (c) are directly or indirectly fused in this order:

(a) two fragments of the non-structural (NS) NS3 protein of the dengue virus (DENV) serotype 1 (DENV1) comprising or consisting of two regions, wherein the first region has the following amino acid sequence:

```
                                              (SEQ ID NO: 1)
ASQEGPLPEIEDEVFRKRNLTIMDLHPGSGKTRRYLPAIVREAIKRKLRT

LILAPTRVVASEMAEALKGMPIRYQTTAVKSEHTGKEIVDLMCHATFTMR

LLSPVRVPNYNMIIMDEAHFTDPSSIAARGYISTRVGMGEAAAIFMTATP

PGSVEAFPQSNAVIQDEERDIPERSWNSGYEWITD,
``` and the second region has the following amino acid sequence:

(SEQ ID NO: 2)
EDHAHWTEAKMLLDNINTPEGIIPALFEPEREKSAAIDGEYRLRGEARKT

FVELMRRGDLPVWLSYKVASEGFQYSDRRWCFDGERNNQVLEENMDVEIW

TKEGERKKLRPRWLDARTYSDPLALREFKEFAAG;

(b) a fragment of the NS4b protein of DENV1 having the following amino acid sequence:

(SEQ ID NO: 3)
VAVENHHHAAMLDVDLHPASAWTLYAVATTIITPMMRHTIENTTANISLT

AIANQAAILMGLDKGWPISKMDIGVPLLALGCYSQV;

(c) a fragment of the NS5 protein of DENV1 having the following amino acid sequence:

(SEQ ID NO: 4)
LDIIGQRIENIKHEHKSTWHYDEDNPYKTWAYHGSYEVKPSGSASSMVNG

VVKLLTKPWDVIPMVTQIAMTDTTPFGQQRVFKEKVDTRTPKAKRGTAQI

MEVTAKWLWGFLSRNKKPRICTREEFTRKVRSNA;

or a polyepitope variant thereof, which (i) comprises or consists of the assembly in a fusion polypeptide, of DENV NS fragments, the sequences of which are obtained by alignment of the NS3 DENV1, NS4b DENV1, NS5 DENV1 fragments recited in (a), (b) and (c) with the respective NS3, NS4b and NS5 sequences of the NS proteins of a virus of the DENV2, DENV3 or DENV4 serotype or (ii) consists of a chimeric polyepitope having an amino acid sequence which has more than 75% identity, in particular more than 80% identity with the sequence of the fusion polypeptide consisting of fused fragments (a), (b) and (c) (from which it derives by mutation of amino acid residues), over its whole length. In particular, said chimeric polyepitope has the amino acid sequence numbered 3, 146, 147 or 148 in the sequence listing of WO2015197565 A1. In particular embodiments, the antigen of DV consists of chimeric DV antigens composed of the fusion of the EDIII polypeptides representative of the four main DV serotypes (DENV1-DENV4), fused to ectoM of DENV1, and in particular has the amino acid sequence numbered 145 in the sequence listing of WO2015197565 A1.

In particular embodiments, the antigen from DV is as disclosed in WO2006136697 A1 (in particular in the claims), in particular the antigen from DV is a chimeric polypeptide comprising a peptide from a subdomain of the E protein of DV bound to a peptide from a subdomain of the M membrane protein of DV.

In particular embodiments, the antigen from WNV or the antigen from DV is selected in the group of:
the heterodimer glycoproteins PreM-E or
a secreted envelope glycoprotein sE or
a polypeptide having at least 80% homology (i.e. sequence identity), or 85% homology or 90% or 95% identity with the polypeptide having the amino acid sequence numbered 5, 6 or 8 in the sequence listing of WO2004076619.

In particular embodiments, the antigen from WNV or the antigen from DV is as disclosed in WO2004076619.

In particular embodiments, the antigen from YFV is an antigen from the YFV 17D strain and/or is the NS1 protein or the ENV protein or a portion of any of these proteins. In particular embodiments, said antigen is as disclosed in WO2004001051 A1, in particular in Example IV.

In particular embodiments, at least one antigen is from a parasite. In particular embodiments, the antigen from a parasite is from a mosquito-borne parasite. In particular embodiments, the antigen is from a parasite such as a *Plasmodium*, in particular *Plasmodium falciparum*. In particular embodiments, the antigen from *Plasmodium falciparum* is a CS (circumsporozoite) protein, also designated as CSP or CSPf, in particular a recombinant CS protein or a fragment thereof.

In particular embodiments, the antigens are from at least two distinct arboviruses, in particular arboviruses specifically disclosed herein, and/or are from at least *Plasmodium falciparum* and an arbovirus. In particular embodiments:
at least one protein antigen is from an arbovirus and at least one vectored antigen is from a parasite;
at least one protein antigen is from a parasite and at least one vectored antigen is from an arbovirus;
at least one protein antigen and at least one vectored antigen are from an arbovirus;
at least one protein antigen and at least one vectored antigen are from the same arbovirus;
at least one protein antigen and at least one vectored antigen are from two distinct arbovirus; and/or
at least one protein antigen and at least one vectored antigen are from a parasite, in particular from *Plasmodium falciparum*.

In particular embodiments, the vectored antigen and the protein antigen are the same antigens. In particular, both the vectored antigen and the protein antigen are the CS protein or an antigen which is a fragment of the CS protein of *Plasmodium falciparum*.

In particular embodiments, at least one vectored antigen is from CHIKV and at least one protein antigen is from *Plasmodium falciparum*, and/or at least one vectored antigen is from *Plasmodium falciparum* and at least one protein antigen is from CHIKV. The antigens from CHIKV and *Plasmodium falciparum* are in particular as described above.

The viral particles are said to be derived from an Measles virus because most of their sequence, and in particular most sequences required for infection and replication of the viral particles, are from the wild-type MV. However, the genomes of the viral particles have several distinctive features over the wild-type MV genome. In particular, the genome of the MV-derived particles comprises a sequence exogenous to MV encoding the antigen, and one or more ATU sequences to enable cloning of the exogenous sequence.

Generally, the genome of the MV-derived particles is a nucleic acid construct comprising the following gene transcription units encompassing from 5' to 3' (antigenome):
(a) a polynucleotide encoding the N protein of a MV;
(b) a polynucleotide encoding the P protein of a MV;
(c) a polynucleotide encoding the M protein of a MV;
(d) a polynucleotide encoding the F protein of a MV;
(e) a polynucleotide encoding the H protein of a MV;
(f) a polynucleotide encoding the L protein of a MV; and the polynucleotide encoding the vectored antigen inserted in an intergenic region, in particular between the P and N coding sequences or between the H and L coding sequences;
said polynucleotides and nucleic acid construct being operably linked and under the control of viral replication and transcription regulatory sequences such as MV leader and trailer sequences. The description of the nucleic acid construct applies to a cDNA encoding the viral antigenomic (+)

RNA. Features above apply to the viral RNA genome, provided that "the polynucleotide encodes the xx protein" is interpreted as "the viral RNA polynucleotide is inverse complementary to an mRNA of the xx protein".

The genes from MV may have mutations relative to the wild-type MV, in particular mutations which reduce infectivity and/or pathogenicity, in particular mutations rendering the virus attenuated. The skilled person is aware that a Measles virus with such mutations would still usually be referred to as an "MV-virus", an "MV-derived virus", an "MV attenuated virus", an "MV vaccine", "MV-derived vaccine", or an "MV attenuated vaccine". The MV-derived virus disclosed herein may therefore also be referred to by these expressions, in particular as an "MV attenuated virus" or an "MV vaccine". The use of the term vaccine does not necessarily imply that a protective immune response is actually obtained when the vaccine is administered; instead, it refers to the fact that particular preferred MV-derived virus strains which are contemplated for use in the present invention are strains used in vaccination methods.

In particular embodiments, the MV-derived viral particles are from an attenuated virus strain, such as a strain used in the art as a commercial and/or approved MV vaccine, such as in particular a strain selected from the group consisting of Schwarz, Moraten, Edmonston-Zagreb and AIK-C strains or selected from the group consisting of CAM-70, TD 97, Leningrad-16, and Shanghai 191 (Ji-191) strains, or from a strain derived from any of these strains, in particular by insertion of a transgene encoding the antigen and/or by any of the modifications described herein. In particular embodiments, the MV-derived viral particle respects the "rule of six" of MV vectors, i.e. its sequence length is a multiple of six nucleotides.

The inventors have shown that insertion of an exogenous sequence, optionally along with deletion of a gene from the MV genome, increased the production of DI genomes from the obtained modified MV vector when it is rescued in a cell. In preferred embodiments, the MV-derived viral particle comprises an exogenous sequence, in particular an exogenous sequence coding for a protein. An exogenous sequence designates a sequence that is not found at the same location in the wild-type MV genome. The sequence encoding the antigen, in particular embodiments where it encodes a non-MV antigen, is such an exogenous sequence. An exogenous sequence may also be an MV sequence, in particular a sequence encoding an antigen from MV, e.g. a gene or a mutated gene from MV or a portion thereof, inserted in a genomic position which is not its position in the wild-type MV (the corresponding endogenous sequence may or may not have been preserved at its position in the wild-type MV).

In a particular embodiment, the MV-derived viral particles in the composition of products of the invention have at least one of the following modifications relatively to the wild-type MV, in addition to the insertion of the sequence coding for the antigen:
  deletion of the C protein or of a portion thereof;
  deletion of the V protein or of a portion thereof;
  deletion of the C and V proteins or of a portion thereof;
  duplication of the N gene or of a portion thereof.

rMV-deltaC (also noted rMV-dC or rMV-4C or or rMV-8C) designates an MV-derived virus wherein the C protein is not expressed, or is not functionally expressed, in particular such a virus wherein the gene coding for the C protein was deleted, in whole or in part, in particular wherein at least 20%, preferably at least 50%, and more preferably at least 70% of the gene sequence was deleted from the viral genome (compared to the wild-type MV) and/or wherein one or several stop codons were introduced in the coding sequence, in particular by insertion (e.g. of a stop codon), deletion (e.g. frameshift deletion) or mutation (e.g. of an amino-acid codon to a stop codon) of 1 to 3 nucleotides. In particular embodiments, the MV-derived viral particles are from rMV-deltaC or from an MV-derived virus wherein the C gene is silenced or deleted as in rMV-deltaC described in the Examples section.

rMV-deltaV (also noted rMV-dV or rMV-4V or rMV-8V) designates an MV-derived virus wherein the V protein is not expressed, or is not functionally expressed, in particular such a virus wherein the gene coding for the V protein was deleted, in whole or in part, in particular wherein at least 20%, preferably at least 50%, and more preferably at least 70% of the gene sequence was deleted from the viral genome (compared to the wild-type MV) and/or wherein one or several stop codons were introduced in the coding sequence, in particular by insertion (e.g. of a stop codon), deletion (e.g. frameshift deletion) or mutation (e.g. of an amino-acid codon to a stop codon) of 1 to 3 nucleotides. In particular embodiments, the MV-derived viral particles are from rMV-deltaV or from an MV-derived virus wherein the V gene is silenced or deleted as in rMV-deltaV described in the Examples section.

rMV-deltaVdeltaC (also noted rMV-dVdC or rMV-4V4C or rMV-8V8C) designates an MV-derived virus wherein none of the C or V protein are expressed, or none are functionally expressed, in particular such a virus wherein the genes coding for the C and V protein were deleted, in whole or in part, and/or wherein one or several stop codons were introduced in the coding sequence as described above. In particular embodiments, the MV-derived viral particles are from rMV-deltaVdeltaC or from an MV-derived virus wherein the both the C and V genes are silenced or deleted as in rMV-deltaV.

rMV-N designates an MV-derived virus wherein a copy of the N gene or a portion thereof was introduced in the virus in addition to the endogenous copy. In particular embodiments, the MV-derived virus is rMV-N or from an MV-derived virus wherein a copy of the N gene or a portion thereof was introduced as in rMV-N described in the Examples section.

In particular embodiments, the MV-derived virus is rMV-CHIKV or rMV-dbp55Gag/Env, as described in the Examples section.

In particular embodiments, the MV-derived viral particles comprise distinct populations of DI genomes, i.e. DI genomes with distinct sequences, in particular with different lengths. In particular embodiments, the MV-derived viral particles comprise at least one population of DI genomes, and in particular each DI population represent at least 0.00001% of the full-length MV genomic RNA in the composition, preferably at least 0.001%, more preferably at least 0.1% and even more preferably at least 1% or 10% of the full-length MV genomic RNA in the composition. % of RNA is intended to mean % in molar content as detected by qRT-PCR.

In particular embodiments, the DI genomes have a length from 200 to 3000 nt, in particular from 400 to 2500 nt. In particular embodiments, the DI genomes in the composition comprise a portion of the sequence of the MV-derived viral particle extending from the nucleotide at position 15800 to the nucleotide at position 15894; in particular embodiments, said portion is present as a double strand. In particular embodiments, the DI genomes in the composition comprise a portion of the sequence of the MV-derived viral particle extending from the nucleotide at position 15600 to the nucleotide at position 15690; in particular embodiments, said portion is present as a single strand. The position in the MV-derived viral particle designates the position of the corresponding nucleotide in the reference MV Schwarz vaccine virus (GenBank AF266291.1), said correspondence being established by aligning the sequences of the MV-derived viral particle and of said reference Schwarz vaccine virus.

The skilled person is aware of methods for producing the viral particles of the composition. In particular, such methods comprise the following steps:
 obtaining or producing a cDNA construct encoding the antigenome of the MV-derived virus;
 transfecting (or otherwise transforming, e.g. transducing) helper cells with one or more helper vectors allowing the expression of the N, P and L proteins of MV and a polymerase, in particular T7 polymerase, or otherwise obtaining helper cells expressing said proteins;
 transfecting (or otherwise transforming, e.g. transducing) said helper cells with said cDNA construct; this step, known as the rescue step, results in the production of particles of the MV-derived virus;
 optionally, co-cultivating said transfected helper cells with "passage cells", suitable for the passage of the MV-derived virus, in particular suitable for the passage of the MV attenuated strain from which said virus was derived and optionally maintaining the passage cells in culture for additional passages, in the presence or in the absence of helper cells;
 recovering the MV-derived viral particles from the culture of helper cells, from the culture of passage cells, or from the co-culture of helper and passaged cells (in particular recovering the supernatant of said cell culture, and/or preparing and recovering the cell lysates).

The method may comprise, in addition to the steps above, a step of recovering the viral particles, optionally purifying and/or quantifying them, and a step infecting passage cells, optionally with a controlled MOI such as an MOI of at least 0.09 or at least 0.1, in particular from 0.0 to 1. Such a step may be performed using viral particles recovered from the helper cells, or from previously infected passage cells (in particular passage cells which were co-cultivated with helper cells). In particular embodiments, the method comprises a step of recovering MV-derived viral particles, titrating said virus and infecting passage cells with a controlled MOI, in particular an MOI in the range defined-herein.

In particular embodiments, the helper cells are human helper cells and in particular are helper cells are from the embryonic kidney cell line 293 (HEK-293), deposited at the ATCC under No. CRL-1573.

In particular embodiments, the passage cells are CEF (chicken embryo fibrobast) as obtained from EARL Morizeau, 8 rue Moulin, 28190 Dangers, France, or from any other producer of fertilized chicken eggs. In particular embodiments, the passage cells are VERO cells, or VERO-hSLAM cells. In particular embodiments, the passage cells are A549 cells.

The inventors have found out that the production of DI particles is increased when cells used for the production of the MV-derived viral particle are infected with a high MOI (multiplicity of infection, designating the ratio of infectious viral particles to target cells), while a high MOI may decrease viral growth. Therefore, the inventors have defined optimal ranges of MOI for the production of MV-viral particles for inclusion in the composition of products of the invention. The inventors have also found out that the production of DI particles is increased when cells have been cultured for several passages.

Accordingly, provided herein are methods to produce the MV-derived viral particles of the composition of products of the invention. Such methods may in particular comprise a step of infecting cells with the MV-derived viral particle at an MOI of at least 0.01, preferably at least 0.05 and even more preferably 0.09 or 0.1 or more; and/or at an MOI of at most 0.3, preferably at most 0.5 and even more preferably at an MOI of 0.1 or less. In particular preferred embodiments, the method comprises a step of infecting cells with an MOI of 0.09 to 1, in particular 0.1. As the skilled person is aware, titrating of viruses entails a certain degree of experimental variation, and a variation of 10% or less of the values above may therefore be acceptable. Accordingly, for example, in particular preferred embodiments, the method comprises a step of infecting cells with an MOI of between 0.09 and 0.11. Such methods may in particular comprise the culture of cells during at least two passages, in particular from 2 to 8 passages prior to vaccine stock preparation, in particular by cell lysis. A passage is understood here as a dilution of the cell culture, usually performed before cells reach confluence, and a passage may therefore be interpreted as maintenance of the cell culture for the period of time required for 2, 3, 5 or 10 cell divisions. In a particular embodiment the MOI for infection is from 0.09 to 1 and the number of passages is from 2 to 8 for the viral stock preparation with the rescued Schwarz MV-derived particles.

In a particular embodiment, the method of producing an MV-derived viral particles comprising DI particles, comprises the steps of:
 a) rescuing recombinant MV-derived viral particles from helper cells transfected with cDNA comprising the antigenome of an MV-derived viral particle, wherein said cells in particular express the N, P and L protein of an MV and an RNA polymerase, in particular T7 polymerase;
 b) recovering the viral particles from the culture of helper cells, or from a co-culture of helper cells with passage cells, i.e. cells suitable for the passage of the MV-derived virus;
 c) infecting passage cells with the MV-derived virus, with an MOI of at least 0.09 and in particular at least 0.1 such as a MOI of 0.09 to 1 to;
 d) recovering MV-derived particles from the culture of passage cells of c).

Another embodiment of the method of producing an MV-derived viral particle comprising DI particles, in particular a method as disclosed above, comprises the steps of:
 a) rescuing recombinant MV-derived viral particles from helper cells transfected with cDNA comprising the antigenome of an MV-derived viral particle, wherein said cells in particular express the N, P and L protein of an MV and an RNA polymerase, in particular T7 polymerase;
 e) infecting passage cells with the MV-derived viral particles, recovered from the helper cells of a), or from cells infected with the viral particles produced from said helper cells, in particular from passage cells co-cultivated with said helper cells;
 f) maintaining the passage cells in culture for at least 3 passages or at least 8 passages and/or for a time sufficient for at least 6 cell divisions, preferably at least 9 cell divisions, and more preferably for at least 15 cell divisions.

In a particular embodiment, in the thus defined method of producing a MV viral stock containing MV-derived viral particles the helper cells are human helper cells such as HEK293T cells or cells derived therefrom and the passage cells are CEF cells, VERO cells, or VERO-hSLAM cells or A549 cells.

The invention also relates to a viral stock which contains rescued MV-derived particles as disclosed herein, in particular MV-derived particles rescued from a vaccine Schwarz strain wherein said particles contain infectious MV-derived particles DI-RNA and/or DI-RNA particles when said rescued MV-derived particles have been passaged on cells such as CEF or Vero cells infected at a MOI of 0.09 to 1 and when the number of passages is at least 2 and in particular from 2 to 10, in particular 8, In particular embodiments, the composition of products of the invention is suitable for in vivo administration, in particular in a human patient. In particular embodiments, the composition is suitable for injection, in particular intravenous, intramuscular or subcutaneous injection. In particular embodiments, the composition is provided as a solution. In particular embodiments, the composition of products of the invention is sterile, in the sense that no other microbiological species is present in the composition, apart from the MV-derived viral particles of the invention. Where the composition of products of the invention comprises several distinct compositions (e.g. for separate, in particular successive, administration), the above may apply to each distinct composition and in particular applies to all of the compositions.

Also provided herein are methods of preventing or treating diseases, in particular infectious diseases related to the antigens of the composition of products of the invention, and/or infection by the MV, using the composition of products of the invention. In such methods, the composition of products of the invention is administered to a patient, in particular to a human patient. Preventing or treating a disease, in particular an infectious disease, is used herein with the usual meaning in the art. In particular, preventing or treating a disease comprises preventing or reducing all or some, in particular the most harmful, of the symptoms of a disease, preventing or limiting microbial infection and/or invasion, etc. While vaccination approaches are commonly used for the prevention of infectious disease, i.e. is used in a patient who has not been infected previously, in some cases vaccination may also be used in an already infected patient in order to treat the infection by stimulating the immune system. Vaccination approaches are commonly used for preventing or treating infectious diseases, but may also be used for non-infectious diseases, in particular for the treatment of cancer, e.g. by stimulating the immune system against an antigen specific to cancer cells.

In particular embodiments, the patient is a human patient. In particular embodiments, the patient is naive relative to the antigens in the composition of products of the invention, i.e. the immune system of the patient has not been presented said antigens prior to the administration of the composition of products of the invention.

In particular embodiments, the composition is for use in the prevention of infectious diseases in a patient, in particular for use in the prevention of infection by an arbovirus and/or for use in the prevention of infection by a parasite, when said arbovirus and/or parasite provide the antigen of the composition of products of the invention. In particular embodiments, the composition is for use in the prevention of at least two distinct infectious diseases, i.e. diseases caused by the infection of at least two distinct species.

The administration scheme in the method of treatment may consist of a single administration, or of several administrations. In the latter case, the administrations may be simultaneous in time and/or separated in time. Simultaneous in time, as used herein regarding administration of compositions or of products of the composition of the invention, means within the same day, preferably within an 8-hour period, preferably within a 1-hour period. Separated in time means on different days, preferably at least 24 hours apart, preferably at least 48 hours apart and more preferably at least one week apart, for example at least four weeks apart.

The treatment of products of the invention may be provided using either as a single composition, which is administered in a single administration, or as a combination of compositions. The combination of compositions may be intended to be administered in a single administration, e.g. if extemporaneous mixture of the compositions is required. Alternatively, the combination of compositions may be intended to be administered in several administrations, simultaneous in time (but, e.g., by distinct administration modes or by injection at distinct locations) and/or separated in time.

The composition of products of the invention is intended to stimulate the immune system against at least two distinct antigens, or against the same antigen provided as both a protein and a coding sequence. As the skilled person is aware, it is often desirable to stimulate the immune system at least twice against a given antigen, both stimulations being separated in time, to obtain efficient immunity against said antigen. "Immunity against an antigen" is used herein to designate the induction of humoral (antibody) or cellular (in particular of CD8+ T-cells) responses against said antigen and/or the capacity of the immune system to prevent infection by a microbe carrying said antigen and/or to target cells carrying said antigen to allow for their killing. Separate administrations of the same antigen in the same patient is usually termed prime-boost administration, with the first administration being the "prime" and the second (and possibly subsequent) administrations being the boost.

It is generally desirable to present an antigen for vaccination in a context of activated innate immune system, as this is thought to favour stimulation of the adaptive immune system. It is therefore common in vaccination methods to administer, together with the antigen, an adjuvant intended to stimulate the innate immune system, in particular through stimulation of type I interferon (IFN) response. The inventors have shown that the DI particles produced by cells producing the MV-derived viral particle are strong stimulators of type I IFN response and may be efficiently used as adjuvants. Therefore, the MV-derived viral particles in the composition of products of the invention, which comprise DI particles, may be used to provide both an antigen (the vectored antigen) and an adjuvant (the DI particles). The DI particles stimulate response to both the vectored antigen and the protein antigen. The composition of products of the invention is preferably administered with no adjuvant in addition to the DI particles. The composition of products of the invention preferably does not comprise traditional adjuvants, in particular does not comprise aluminium salts or gels, monophosphoryl lipid A or squalenes such as AS03.

In prime-boost administration schemes, the presence of an adjuvant is particularly preferred in the priming composition.

In particular, the method of preventing or treating may comprise two administrations, separated in time, in particular an administration for priming and an administration for boosting the immune response. In particular embodiments, the MV-derived viral particles are administered at least at the priming step. In particular embodiments, at least the MV-derived viral particles and the protein antigen are administered at the priming step. In particular embodiments, at least the protein antigen is administered at the boosting step. In particular embodiments, the vectored antigen is administered at the boosting step, either within a vector coding the antigen, in particular the MV-derived viral particles used for priming, or in another presentation, in particular as a recombined and/or purified protein.

In certain embodiments, the composition is for use in the prevention of an infectious disease in a patient, in an administration scheme wherein the MV-derived viral particles are administered simultaneously in time with the recombinant protein. In certain embodiments, the administration scheme comprises a priming and a boosting administration and both the MV-derived viral particles and the protein antigen are administered in the priming administration. In certain of such embodiments, the boosting administration comprises the administration of (i) the MV-derived viral particles, or of (ii) the protein antigen, or of (iii) both the MV-derived viral particles and the protein antigen.

The vectored antigen may be administered, in addition to the administration of the MV-derived virus triggering expression of said antigen, as a protein. As mentioned above, the composition of the invention may indeed comprise the same antigen present as both the vectored antigen (or one of the vectored antigens) and the protein antigen (or one of the protein antigens). In particular, the priming administration may comprise the administration of the same antigen as both a vectored antigen and a protein antigen. It is similarly possible that an antigen is provided in one administration as a vectored antigen and in another administration as a protein antigen. In particular, the same antigen may be provided in the priming step as a vectored antigen and in the boosting step as a protein antigen.

In certain embodiments, the composition is for use in the prevention of an infectious disease in a patient, in an administration scheme wherein the MV-derived viral particles are administered to prime the immune response to an antigen and the protein antigen is administered to boost the immune response to said antigen and/or to prime the immune response to another antigen.

In certain embodiments, the composition is for use in the prevention of an infectious disease in a patient, in an administration scheme wherein the MV-derived viral particles are administered to stimulate the innate immune response, and to prime the adaptive immune response to an antigen, and the protein antigen, being in particular a recombinant protein, is administered to prime an adaptive immune response to a second antigen, preferably in conditions of activated innate immunity.

In certain embodiments, the administration scheme comprises:

a priming step comprising the administration of a composition of products of the invention, comprising MV-derived viral particles comprising a first antigen as a vectored antigen and a second antigen as a protein antigen; and a boosting step comprising the administration of:

a composition, in particular a composition of products of the invention, comprising MV-derived viral particles comprising the first antigen as a vectored antigen and the second antigen as a protein antigen; or a composition comprising the first antigen as a protein antigen; or a composition comprising the second antigen as a protein antigen; or a composition comprising both the first and second antigen as protein antigens.

In the above methods, the first antigen, administered in the prime as a vectored antigen, may be administered in the boosting step as a protein antigen, in particular as a recombinant protein encoded by the same nucleic acid sequence which encodes the first antigen in the MV-derived viral vector. The vectored antigen and the protein antigen may also be both from the same protein, with overlapping sequences, but not necessarily with strictly the same size and/or sequence, in particular the protein antigen may be a portion of the vectored antigen or the vectored antigen may be a portion of the protein antigen.

In certain embodiments of any of the methods above involving a priming and a boosting administration, said administrations are separated by at least four weeks, in particular by at least 6 weeks, in particular by at least 12 weeks.

In another embodiment, the invention also relates to the use of DI-RNA of a measles virus genome as described herein as an adjuvant in an immunogenic composition, in particular in a composition as disclosed above or in the examples to enhance the immune response.

LEGENDS OF FIGURES

FIG. 1. Detection of DI-RNAs produced by rMV.

(A) Schematic representation of 5' copy-back DI-RNA generation by the viral polymerase (RdRp). Primers used for PCR are represented. (B) Total RNA was extracted 24 hours post-infection with MV-Schwarz, rMV-N, rMV-$\Delta$V and rMV-$\Delta$C at a MOI of 1. DI-RNAs and genomes were detected by RT-PCR in four different cell types (A549, HeLa, 293T, Vero).

Figure 2:
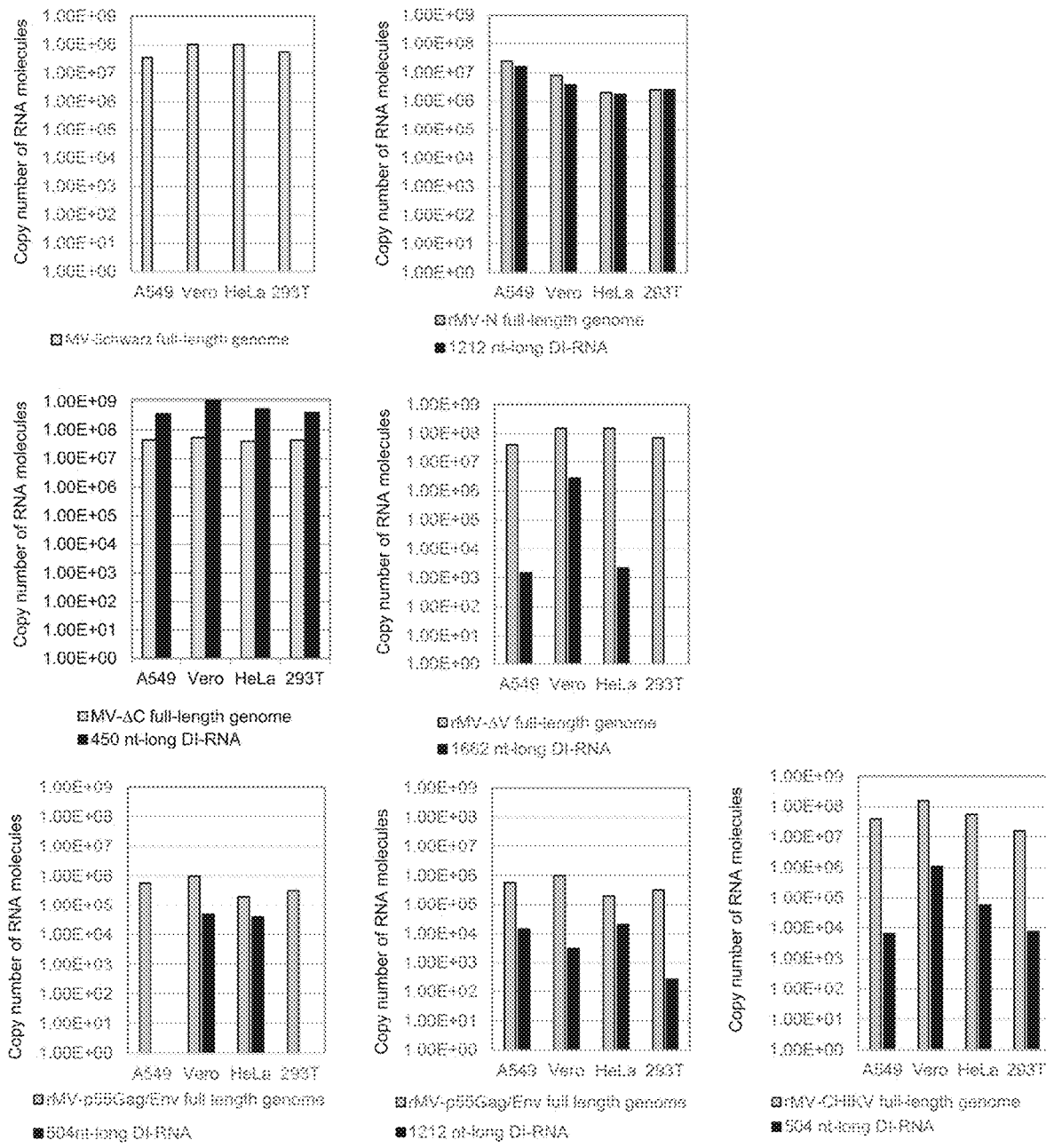

FIG. 2. Absolute quantification of genomes and DI-RNAs for MV-Schwarz, rMV-N rMV-$\Delta$V, rMV-$\Delta$C, rMV-CHIKV and rMV-p55Gag/Env in four different cell lines.

Total RNA (400 ng) purified from 24 hours post-infection cells was analyzed by RT-qPCR. Absolute quantification was performed using serial dilutions of in vitro transcribed MV DI-RNAs or MV genome RNA fragment. Results are expressed in copy number of RNA molecules. Samples were tested in triplicates.

FIG. 3. IFN response to rMVs on A549 and STING-37 cells.

(A) Growth curves of MV-Schwarz, rMV-N, rMV-$\Delta$V, rMV-$\Delta$C, rMV-CHIKV and rMV-p55Gag/Env during 60 hours after A549 cells infection at a MOI of 1. Titres are expressed in $TCID_{50}$/ml. (B) IFN-$\beta$ mRNA and (C) Mx1 mRNA fold induction 12, 24 and 36 hours post-infection of A549 cells at a MOI of 1. Quantification of mRNA was done by RT-qPCR gene expression assay. (D) IFN-$\beta$ mRNA fold induction 12, 24 and 36 hours post-infection of A549 cells infected by UV-inactivated (UV-in.) rMV. (E) Luciferase reporter activity of STING 37 cells infected by rMVs at a MOI of 1 during 36 hours. IFN-$\alpha$ at 500 UI/ml was used as positive control, non-infected cells (mock) as negative control. Experiments were performed two times and data represent means±SD of the technical triplicates of the most representative experiment.

Figure 4A:
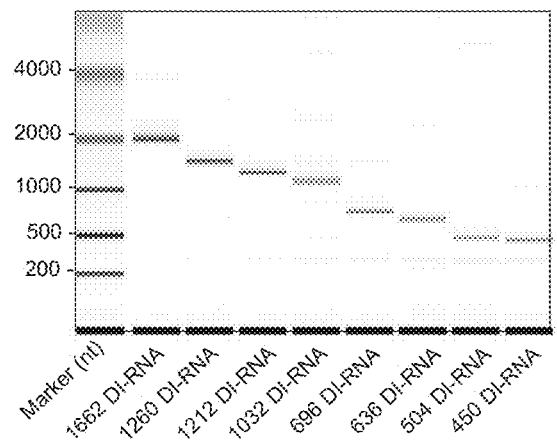

FIG. 4. IFN response to DI-RNAs transfection on STING-37 and A549 cells.

STING-37 and A549 cells were transfected with 10 ng of eight in vitro transcribed DI-RNAs of different lengths, actin RNA, Poly I:C of high molecular weight (HMW) or low molecular weight (LMW) and 5' triphosphate RNA (5'3P). (A) in vitro transcribed DI-RNAs analysis on Agilent bioanalyzer. (B) Luciferase reporter activity of STING-37 cells and (C) IFN-β mRNA expression profile in A549 cells were measured 24 hours post-transfection and normalized to mock transfected cells. Experiments were performed three times and data represent means±SD of the technical triplicates of the most representative experiment.

Figure 5:
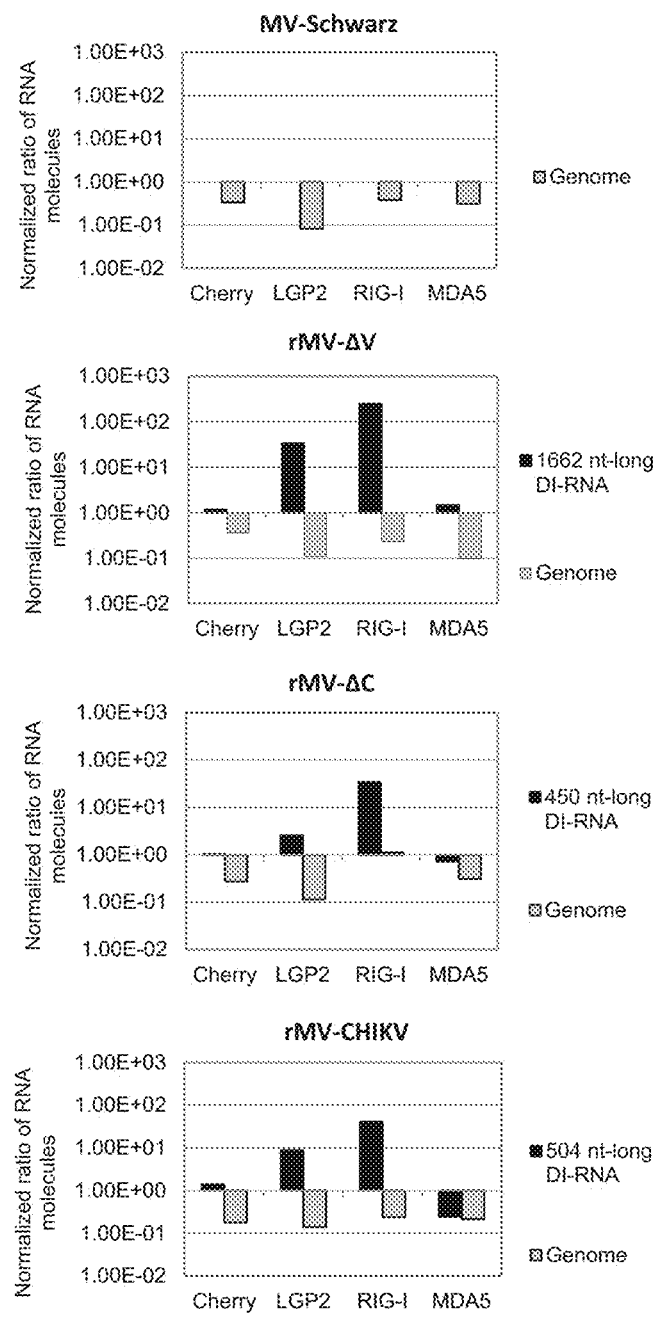

FIG. 5. 5' copy-back DI-RNAs specific binding to Rig-I like receptors.

Ratio of genomes and DI-RNA molecules after to before One-STrEP tag affinity purification of ST-RLR cell lines. 10 ng of either total RNA and RNA obtained after affinity chromatography of STrEP tagged Cherry (negative control), LGP2, RIG-I and MDA5 was analyzed by RT-qPCR. Absolute quantification was performed as described for FIG. 2. Samples were analyzed in triplicates and two biological replicates were performed.

FIG. 6. 504 nucleotide-long 5' copy-back DI-RNA of rMV-CHIKV.

(A) Total RNA was extracted 24 hours post-infection by rMV-CHIKV and rMVp55Gag/Env at a MOI of 1. DI-RNAs were detected by RT-PCR in Vero cells. (B) Schematic representation and exact nucleotide sequence of 504 nt-long DI-RNA of rMV-CHIKV (SEQ ID NO: 26).

Figure 7:
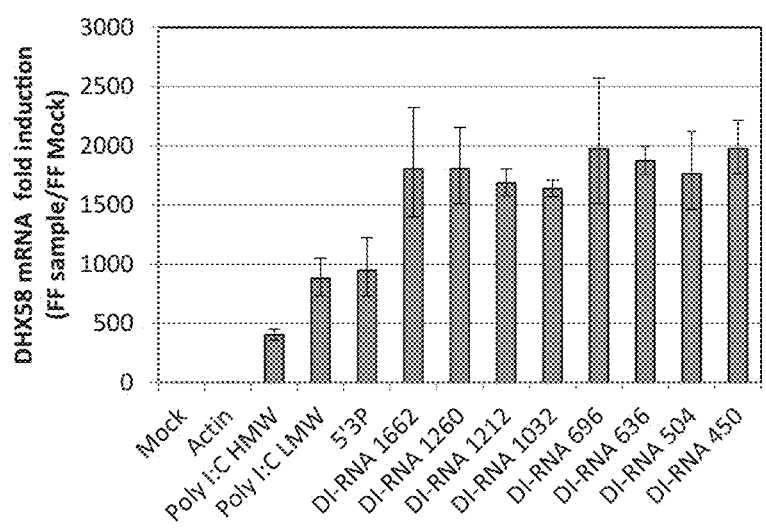

FIG. 7. Expression profile of DHX58 mRNA in A549 cells transfected with in vitro transcribed DI-RNAs.

A549 cells were transfected with 10 ng of eight in vitro transcribed DI-RNAs of different lengths, actin RNA, Poly I:C of high molecular weigh (HMW) or low molecular weigh (LMW) and 5' triphosphate RNA (5'3P). DHX58 mRNA were measured by qRT-PCR 24 hours post-transfection and results were normalized to mock-transfected cells. Experiments were performed three times and data represent means±SD of the technical triplicates of the most representative experiment.

Figure 8:
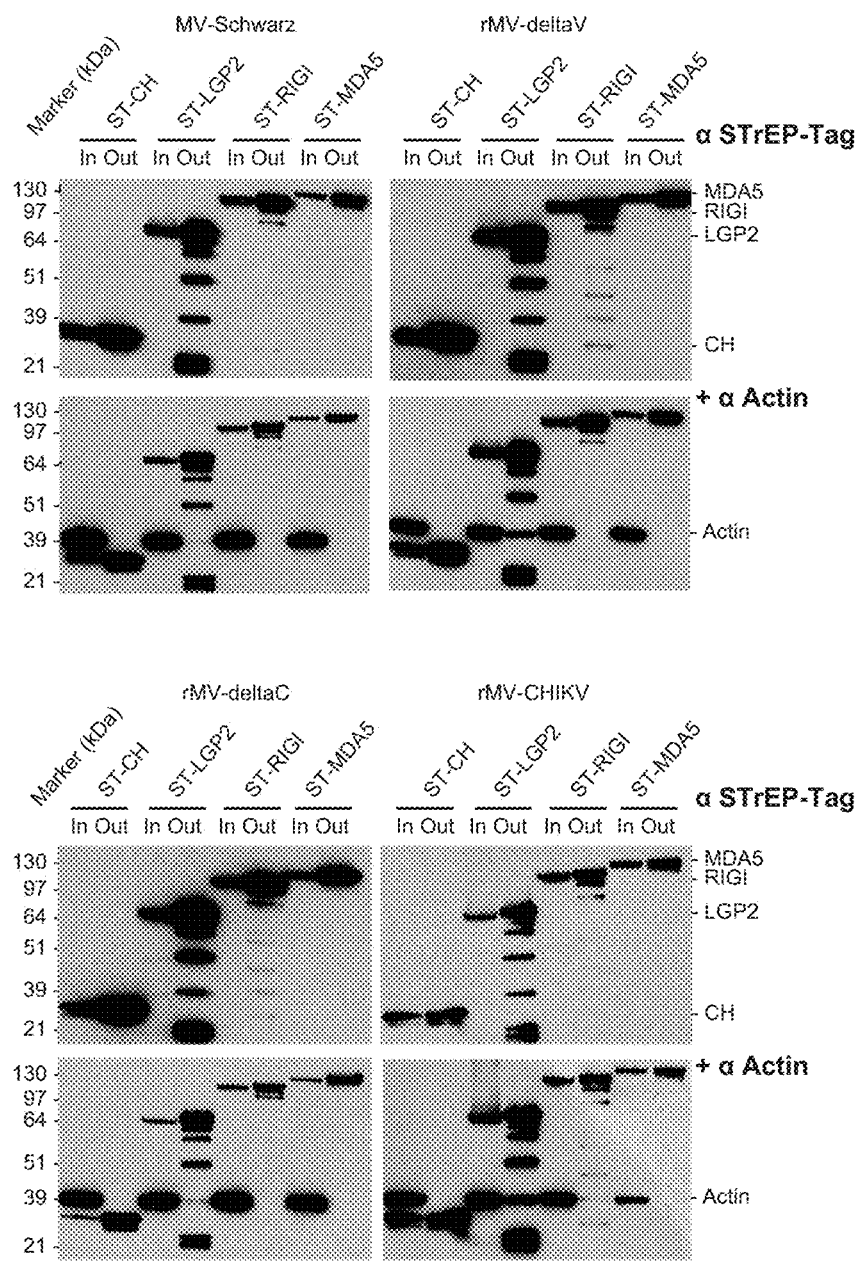
Figure 9A:
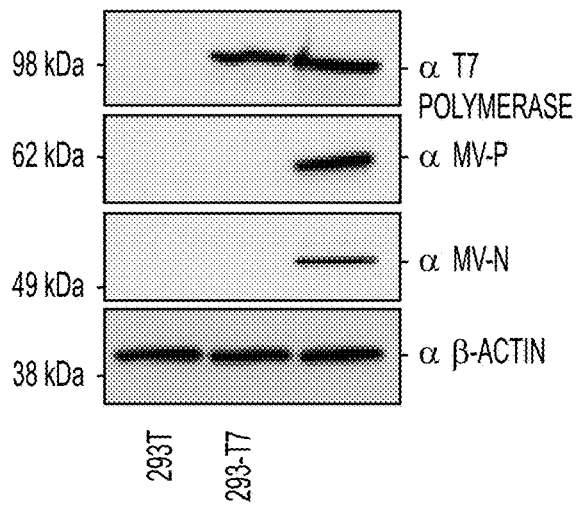
Figure 9B:
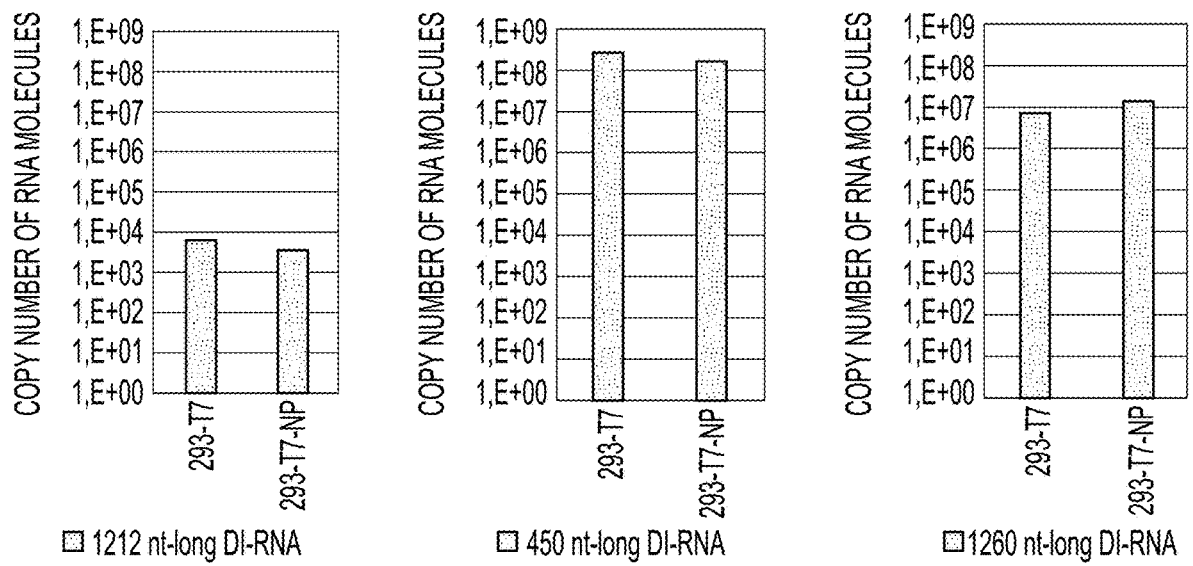
Figure 9C:
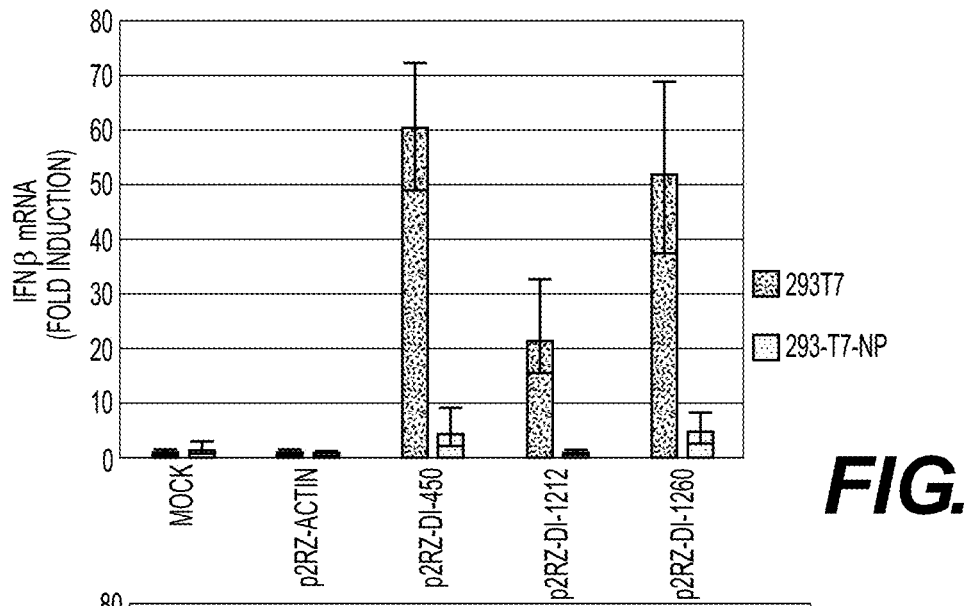
Figure 9D:
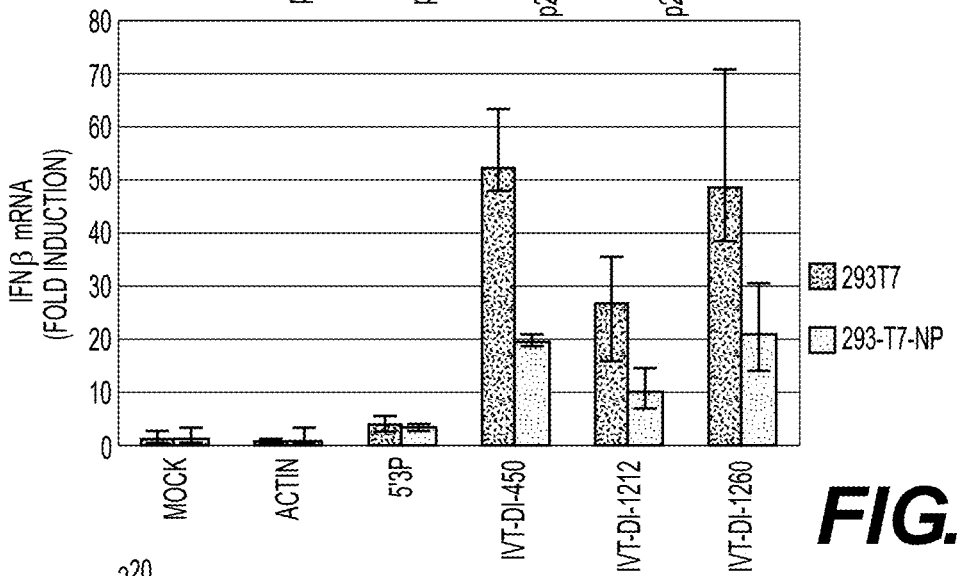

FIG. 8. Western Blot of infected ST-RLR before (input) and after (output) One-STrEP tag affinity purification.

β-actin served as negative control.

FIG. 9: Analysis of type-I IFN activation by MV DI-RNAs in the presence of MV-N and P proteins. (A) Western Blot analysis of T7 polymerase, MV-N, MV-P and β-actin in HEK293-T7 and HEK293-T7-NP cell lysates. (B) Absolute quantification of 1212, 450 and 1260 nt-long MV DI-RNA produced by HEK293-T7 and HEK293-T7-NP cells transfected with p2RZ-DI 1212, 450 and 1260 vectors. Total RNA (400 ng) purified from cells 24 hours after transfection was treated with RQ1 DNase RNase-free and 100 ng was analysed by RT-qPCR. Absolute quantification was performed using serial dilutions of in vitro transcribed MV DI-RNAs and normalized with actin. Results are expressed in copy number of RNA molecules. Experiments were performed two times and samples were tested in triplicates. (C-D) HEK293-T7 and HEK293-T7-NP cells were transfected with either (C) vector p2RZ encompassing DI-RNAs or actin sequence or (D) in vitro transcribed RNAs (Actin, 5'3P or 3 different IVT DI-RNAs). Relative IFN-β mRNA expression was measured 24 hours post-transfection and normalized to GAPDH and compared to mock transfected cells. Experiments were performed two times and data represent means±SD of the technical triplicates of the most representative experiment.

Figure 10:
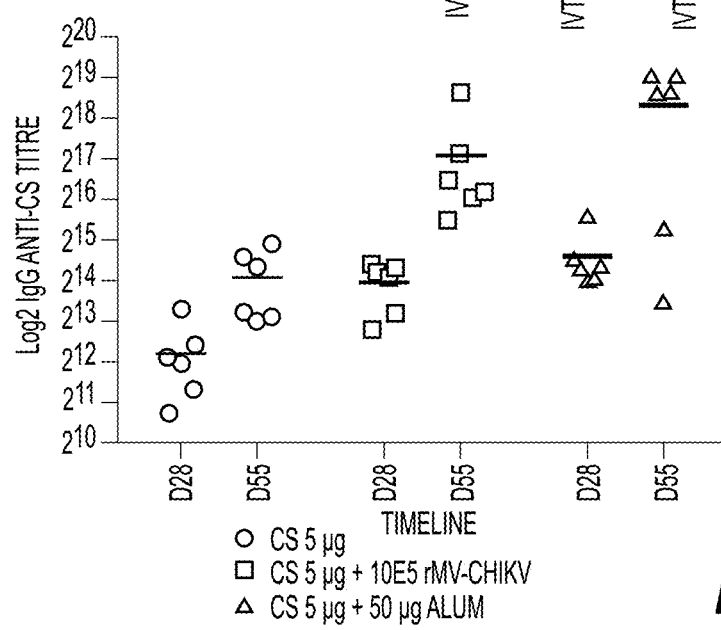

FIG. 10: CS antibody response elicited in C57BL/6 mice. (A) IgG anti-CS titre in mice immunized with CS alone (blue) or with rMV-CHIKV (purple) or with alum (red, positive control) at day 28 (before the second immunization) and day 55 (4 weeks after the second immunization). Antibody titres are expressed in Log 2. (Below) IgG antibody titre at day 55

| | CS 5 µg | CS5 µg + rMV-CHIKV | CS 5 µg + Alum |
|---|---|---|---|
| Day 55 | 1,70E+04 | 1,38E+05 | 3,29E+05 |

Figure 11:
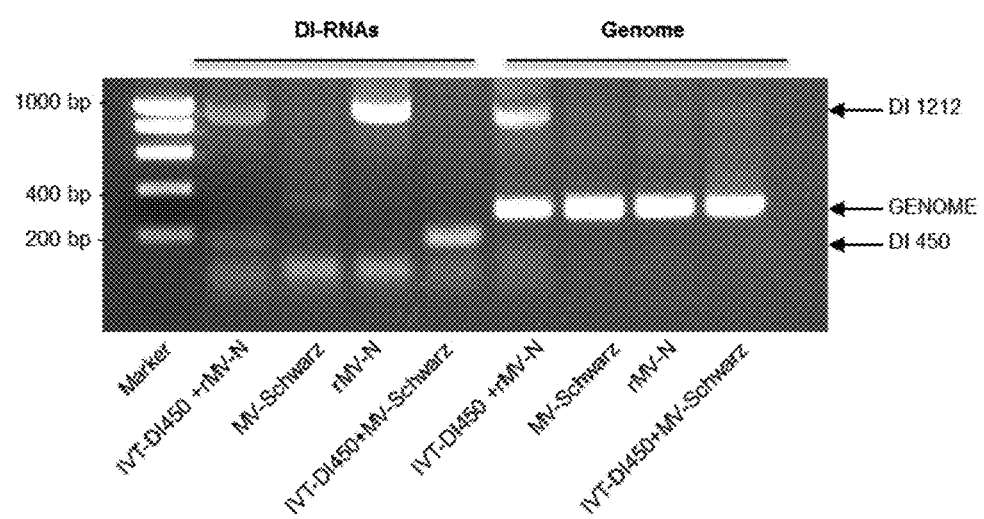

FIG. 11: Detection of Genome and DI-RNAs in Vero cells infected at a MOI of 1 with viral stocks resulting from a transfection of IVT-DI-RNA 450 followed by MV-Schwarz or rMV-N infection in HEK293T cells. Total RNA was extracted 48 hours post-infection. DI-RNAs and genomes were detected by RT-PCR

EXAMPLES

Example 1. Cells and Viruses

HEK-293T (human embryonic kidney cells), Vero (African green monkey kidney cells), A549 (adenocarcinomic human alveolar basal epithelial cells) and HeLa cells were maintained in Dulbecco's modified Eagle medium (#10566-016, Gibco™ DMEM) supplemented with 10% heat-inactivated fetal calf serum (#A15-101, GE Healthcare) and 10,000 U/ml of Penicillin-Streptomycin (#15140122, Life Technologies). Vero-SLAM (and HEK-293 cell lines expressing One-STrEP-tagged RIG-I (ST-RIG-I), MDA5 (ST-MDA5), LGP2 (ST-LGP2) and Cherry (ST-CH) (13) were maintained with the same medium supplemented with G418 (#G8168, SIGMA) at 500 µg/ml. The STING-37 cell line corresponded to HEK-293 cells stably transfected with an ISRE-luciferase reporter-gene (25).

The MV-Schwarz vaccine strain (26) and seven recombinant MVs, rMV-N expressing an additional nucleoprotein in ATU 2 (10), rMV-ΔC lacking MV protein C (27) and rMV-ΔV lacking MV protein V (13), rMV-CHIKV expressing five chikungunya structural proteins (E1, E2, E3, C and 6K) in ATU 2 (28), rMV-p55Gag/Env expressing the p55Gag polyprotein and the EnvΔV1V2 envelope glycoprotein in ATU2 (29), rMV-GFP expressing green fluorescent protein in ATU2 and rMV-CH expressing Cherry red fluorescent protein in ATU3 were used. Wild-type MV (wt-MV) was obtained from a urine patient sample. Stock of wt-MV was obtained by virus multiplication on Vero-SLAM cells at a MOI of 0.1.

Virus titres were determined by 50% $TCID_{50}$ titration on Vero cells (or Vero-SLAM cells for wt-MV). Two different viral stocks from two technical replicates of rescues were obtained for rMV-ΔC, rMV-N and rMV-CHIKV using the protocol described by Radecke et al. (30) and modified by Parks et al. (31).

Example 2. Virus Growth Curves

Monolayers of A549 cells of 24-mm-diameter-dishes (6-well-plates) were infected with MV-Schwarz or rMVs at a MOI of 1. At various times post-infection, cells were scraped into culture medium. After freeze thawing of cells and medium, and clarification of cell debris, virus titres were determined. For this purpose, Vero cells were seeded into 96-well plates (7500 cells/well) and infected by serial 1:10 dilutions of virus sample in DMEM-5% FCS. After incubation for 7 days, cells were stained with crystal violet and the TCID$_{50}$ values were calculated by use of the Karber (1931) method.

Example 3. Virus Infection for RT-PCR Detection of 5' Copy-Back DI-RNAs

Cells were seeded into T25 flasks one day before infection. Virus infections were carried out with a MOI of 1. Viruses were diluted with Opti-MEM to obtain a final inoculum volume of 2 ml. Cells were incubated with virus for 2 hours at 37° C. Then, 4 ml of DMEM containing 10% FBS were added in each T25 flask, and cells were incubated at 37° C. until infections were stopped by cell lysis 24 hours later.

Total RNA was extracted with RNeasy mini kit (#74104, Qiagen). cDNA was generated from 300 ng of total RNA using Superscript III (#18080-093, Thermo Fisher Scientific) and primer A2 (Table 1) in a total volume of 20 µl. A total of 2 µl of the resultant cDNA was then amplified with primers A2 and JM402 (Table 1) for genome amplification, A2 and JM403 (Table 1) for DI-RNA amplification, using Phusion® High-Fidelity DNA Polymerase (#F-5305/L, Thermo Fisher Scientific) in a total volume of 50 µl (95° C. for 2 min; 40 cycles of 95° C. for 30 sec, 55° C. for 30 sec, 72° C. for 1 min; 72° C. for 10 min). At the end of the PCR, Taq DNA polymerase (#10342-053, Thermo Fisher Scientific) was added and incubated at 72° C. for 10 min. The products were analyzed on a 1% agarose gel with Smartladder (#MW-1700-10, Eurogentec) as the size standard, and gel purified with QIAquick® Gel Extraction Kit (#28704, Qiagen). The PCR-amplified products were cloned into pTOPO vector (#45-0640, Thermo Fisher Scientific) and sequenced.

Table 1

| PCR primer | 5' - 3' sequence |
|---|---|
| RT-PCR Primers and probes used in the study | |
| A2 (Pfaller, 2014) | AAAGCTGGGAATAGAAACTTCG (SEQ ID NO: 5) |
| JM 403 (Shingai, 2007) | CGAAGATATTCTGGTGTAAGTCTAGTA (SEQ ID NO: 6) |
| JM 402 (Shingai, 2007) | TTTATCCAGAATCTCAATCCGG (SEQ ID NO: 7) |

TABLE 2

Characterisation of DI-RNAs produced by different MV.

| virus | Rescue | DI-RNA Length (nt) | Breakpoint site[1] | Re-initiation site[1] | ssRNA loop (nt) | dsRNA stem (nt) | Indels (nt) | Rule of six |
|---|---|---|---|---|---|---|---|---|
| MV-Schwarz | a | — | — | — | — | — | — | — |
| rMV-N | a | 1212 | 14781 | 15797 | 1016 | 98 | — | 202 × 6 |
|  | b | 1140 | 14895 | 15755 | 860 | 140 | — | 190 × 6 |
| rMV-ΔV | a | 1662 | 14428 | 15696 | 1264 | 199 | — | 277 × 6 |
|  |  | 1260 | 14793 | 15737 | 938 | 161 | — | 210 × 6 |
| rMV-ΔC | a | 1440 | 14648 | 15702 | 1054 | 193 | — | 240 × 6 |
|  |  | 450 | 15557 | 15783 | 226 | 112 | — | 75 × 6 |
|  | b | 2094 | 13946 | 15750 | 1804 | 145 | — | 349 × 6 |
|  |  | 1032 | 15046 | 15712 | 666 | 183 | — | 172 × 6 |
|  |  | 696 | 15302 | 15792 | 490 | 103 | — | 116 × 6 |
|  | c | 1218 | 14839 | 15733 | 894 | 162 | — | 203 × 6 |
|  |  | 636 | 15351 | 15803 | 452 | 92 | — | 106 × 6 |
| rMV-GFP | a | 402 | 15591 | 15797 | 206 | 98 | — | 67 × 6 |
| rMV-CH | a | 978 | 15062 | 15750 | 688 | 145 | — | 163 × 6 |
| rMV-CHIKV | a | 504 | 15521 | 15765 | 244 | 130 | — | 84 × 6 |
|  |  | 1260 | 14793 | 15737 | 938 | 161 | — | 210 × 6 |
|  | b | 462 | 15530 | 15798 | 268 | 97 | — | 77 × 6 |
| rMV-p55Gag/Env | a | 504 | 15542 | 15744 | 202 | 151 | — | 84 × 6 |
|  |  | 1212 | 14781 | 15797 | 1016 | 98 | — | 202 × 6 |
| Wild type | — | 1212 | 14781 | 15797 | 1016 | 98 | — | 202 × 6 |

[1]nucleotide positions of breakpoints and reinitiation sites as aligned to the reference sequence for Schwarz vaccine virus (GenBank: AF266291.1)

Example 4. TaqMan RT-qPCR Analysis of DI-RNAs and Full-Length MV Genomes

The analysis was performed using Applied Biosystem StepOnePlus™ technology. Various MV DI-RNAs primers and probes were designed using Primer Express Software (Applied Biosystem) (Table 3). Reactions were performed on 400 ng of total RNA using TaqMan RNA-to-Ct 1-Step Kit (#4392938, Thermo Fisher Scientific) for one-step RT-qPCR analyses. Reactions were performed in a final volume of 20 µl in the presence of 100 nM of each TaqMan DI-RNA specific probe and 100 nM of each DI-RNA specific forward and reverse primers. For absolute quantification of DI-RNAs, standard curves were established using serially diluted RNAs obtained by in vitro transcription of plasmids encompassing DI-RNAs specific for each rMVs. The DI-RNAs sequences were cloned into the in vitro transcription vector P2RZ (#27664, Addgene) with HindIII and NheI restriction sites. In vitro transcription was carried out at 37° C. using T7 RiboMAX™ (#P1320, Promega), and RNA products were purified using RNeasy clean up (#74104, Qiagen). Protocol for absolute quantification of β-actin or MV genome was described elsewhere (10). The standard curves were generated by the StepOnePlus™ software system by plotting the Cts against the logarithm of the calculated initial copy numbers. The unknown initial sample copy numbers were then automatically calculated from their Cts, as compared with the RNA standard curves.

TABLE 3

RT-qPCR primers and probes used in the study

| Targeted RNA | 5' - 3' sequence:<br>Forward primer<br>Reverse primer<br>TaqMan probe (reporter dye) |
|---|---|
| Measles genome | TCAGGCATACCCACTAGTGTGAA<br>(SEQ ID NO: 8)<br>TGACAGATAGCGAGTCCATAACG<br>(SEQ ID NO: 9)<br>CATCAGAATTAAGAAAAACGTAG<br>(SEQ ID NO: 10) (VIC) |
| β-actin | ACCGAGCGCGGCTACAG<br>(SEQ ID NO: 11)<br>CTTAATGTCACGCACGATTTCC<br>(SEQ ID NO: 12)<br>CACCACCACGGCCGA<br>(SEQ ID NO: 13) (FAM) |
| 504 nt-long DI-RNA | CGGAGTTCAACCAATTAGTCCTTAA<br>(SEQ ID NO: 14)<br>TGTGCCCCCAGAATTTGC<br>(SEQ ID NO: 15)<br>CAGGGCACTATCTAGG<br>(SEQ ID NO: 16) (FAM) |
| 1212 nt-long DI-RNA | TTGCAAATAATGCCTAACCACCTA<br>(SEQ ID NO: 17)<br>ACACTGCCTACCCACGTGACT<br>(SEQ ID NO: 18)<br>CAGGATTAGGGTTCCGGG<br>(SEQ ID NO: 19) (FAM) |
| 1662 nt-long DI-RNA | TTACCTTAAAAACCCACTCACGTTT<br>(SEQ ID NO: 20)<br>AGATTGCCCCCTGAAATGG<br>(SEQ ID NO: 21)<br>AACACAAGCAAGCACA<br>(SEQ ID NO: 22) (FAM) |
| 450 nt-long DI-RNA | TTATCAACTTTTTGTTCCCGGAGTA<br>(SEQ ID NO: 23)<br>ACCACCTAGGGCAGGATTAGG<br>(SEQ ID NO: 24)<br>AGATAATTGGTTGAACTCCGGAA<br>(SEQ ID NO: 25) (FAM) |

Example 5. Affinity Chromatography of RLR RNP Complexes and Subsequent RNA Purification ST-RLR cells ($4\times10^7$) were infected at a MOI of 1 for 24 h by MV-Schwarz, rMV-ΔV, rMV-ΔC and rMV-CHIKV. Cells were washed twice with cold PBS and lysed in 4 ml of lysis buffer (20 mM MOPS-KOH pH7.4, 120 mM of KCl, 0.5% Igepal®, 2 mM β-Mercaptoethanol), supplemented with RNasin® at 1/200 (#N2515, Promega) and Complete Protease Inhibitor Cocktail (#11873580001, Roche). Cell lysates were incubated on ice for 20 min with gentle mixing every 5 min, and then clarified by centrifugation at 16,000 g for 15 min at 4° C. A 100-µl aliquot of each cell lysate was used to perform total RNA purification using TRI Reagent LS (#T3934, Sigma). The rest of cell lysate was incubated for 2 hours on a spinning wheel at 4° C. with 200 µl of Strep-Tactin® Sepharose High Performance (#28-9355-99, GE Healthcare). Beads were collected by centrifugation (1,600 g for 5 min at 4° C.) and washed three times for 5 min on a spinning wheel with 5 ml of washing buffer (20 mM MOPS-KOH pH7.4, 120 mM of KCl, 2 mM β-Mercaptoethanol) supplemented with RNasin® at 1/400 and Complete Protease Inhibitor Cocktail. RNA purification was performed using TRI Reagent LS. RNA was dissolved in 50 µl of DNase-free and RNase-free ultrapure water. Extracted RNAs were analyzed using Nanovue (GE Healthcare) and Bioanalyser RNA nano kit (#5067-1511, Agilent).

To validate the efficacy of RLR ribonucleoprotein complex purification protein extracts were resolved by SDS-polyacrylamide gel electrophoresis on 4-12% Criterion™ gels BioRad) with MOPS running buffer and transferred to cellulose membranes (GE Healthcare) with the Criterion™ Blotter system (BioRad). The following antibodies were used: an anti-STrEP-Tag (#34850, Qiagen), anti-LGP2 (#NBP1-85348, Novus), anti-MDA5 (#5321, Cell Signaling), anti-RIG-I (#D14G6, Cell Signaling) or monoclonal anti-β-actin antibody (#A5441, Sigma).

Absolute quantification of DI-RNAs, genomes and β-actin mRNA was done by RT-qPCR on total RNA and on RNA obtained after One-STrEP tag affinity purification. β-actin mRNA was used to normalise the quantity of RNA before to after affinity purification.

Example 6. Analysis of rMVs Immunostimulatory Activity

STING-37 cells (25), stably transfected with an ISRE-luciferase reporter-gene, were infected by MV-Schwarz and different rMVs at a MOI of 1, were non-infected (Mock), or were transfected with 10 ng of in vitro transcribed DI-RNAs, using TransIT®-mRNA Transfection Kit (#MIR2250, Mirus). Cells were lysed at different time points post-infection. The Firefly luciferase activity was measured using the Bright-Glo™ Luciferase Assay System (#E2650, Promega) following the manufacturer's recommendation.

Example 7. TaqMan RT-qPCR of β-IFN and ISG Expression

Gene expression qPCR analysis was performed using the Applied Biosystem StepOnePlus™ technology. Total RNA was extracted from A549 cells infected by different rMVs at different time points using the RNeasy Mini Kit (#74104, Qiagen). Expression levels of IFNβ or ISG (Mx1 and DHX58) were quantified by one-step real-time PCR using GAPDH mRNA expression as internal control. Hundred ng of total RNA was amplified with 20× custom TaqMan Gene Expression Assays (#Hs01077958_s1; #Hs00895608_m1; #Hs00225561_m1; #Hs99999905_m1) using TaqMan RNA-to-Ct 1-Step Kit in accordance with the manufacturers' instructions. All the measurements were performed in triplicate and analysed as generated by StepOnePlus™ software system.

Example 8. Various 5'Copy-Back DI-RNAs are Produced by Modified Recombinant MVs

Figure 1B:
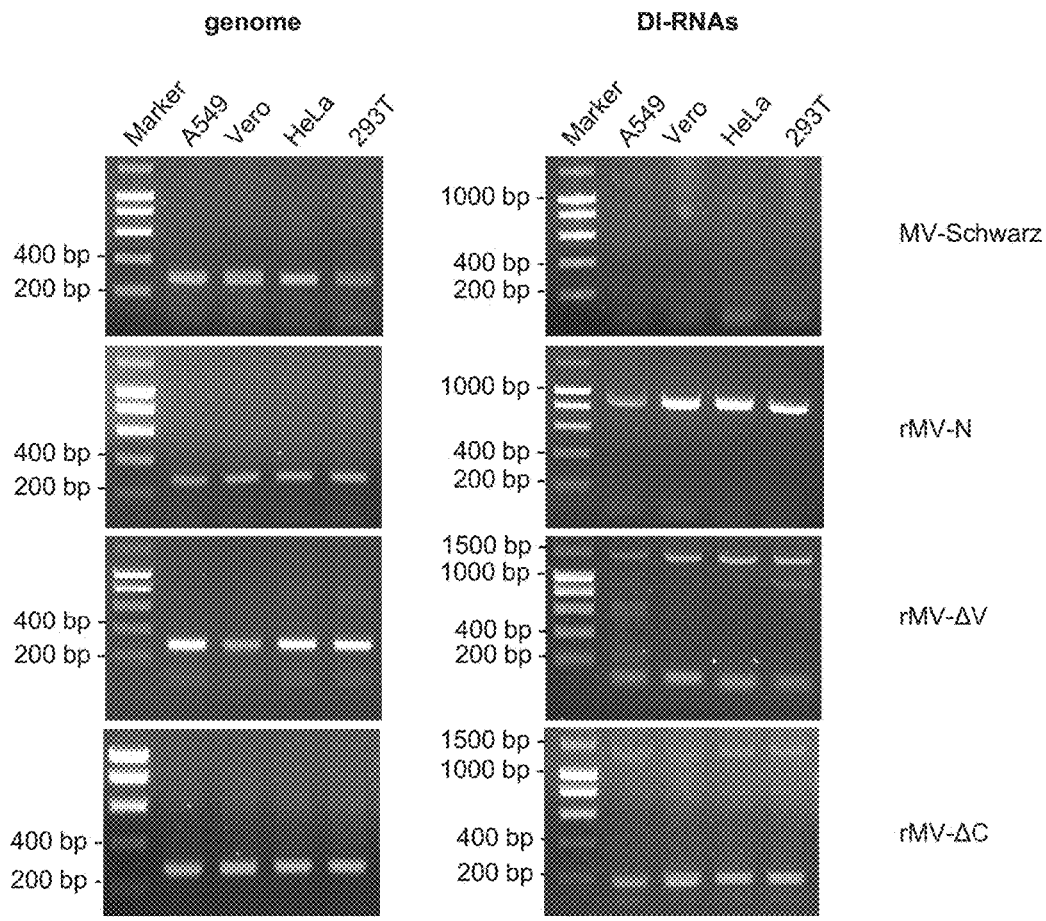

Production of 5' copy-back DI genomes has previously been shown for three modified rMVs, separately in independent studies: rMV-N (10), rMV-ΔV (13) and rMV-ΔC (23). By applying a unique RT-PCR protocol, we performed molecular characterization and studied profiles of 5'copy-back DI-RNAs produced by rMV-N, rMV-ΔV and rMV-ΔC in parallel and in four different cell types. MV-Schwarz, from which rMVs are derived, was used as a negative control for the DI genome production. DI genomes were detected by RT-PCR using two primers both of negative polarity in accordance to the full-length MV genome, so that only 5' copy-back DI-RNAs could be amplified (FIG. 1A and Table 1). DI genomes presence was assessed 24 hours post-infection of Vero, A549, 293T and HeLa cells at a MOI of 1 on total RNA purified from infected cells. As expected, we observed that various DI-RNAs were produced upon infection with modified rMVs but not the control MV-Schwarz strain (FIG. 1B).

Further, we performed molecular characterization of various 5'copy-back DI-RNAs produced upon infection with rMV-N, rMV-ΔV and rMV-ΔC. Thus, cDNA molecules encompassing the corresponding DI genome fragments were extracted from agarose gel, cloned, amplified, sequenced and aligned on MV-Schwarz sequence. Then, the known structure of 5'copy-back DI genome allowed deduction of the entire sequence of the DI-RNA from the amplified cDNA. Table 2 summarizes important points that define each 5' copy-back DI-RNAs: the breakpoint site corresponds to the last nucleotide incorporated by the RdRp before leaving the template antigenome strand; the re-initiation site corresponds to the first nucleotide where the polymerase begin the synthesis of a complementary RNA strand of opposite polarity. We validated that rMV-N produced a single population of 1212 nt-long DI-RNA (10). rMV-ΔV produced two DI-RNAs of 1662 and 1260 nt-long, and rMV-ΔC one major DI-RNA of 2094 nt-long, but also minor DI-RNAs of different sizes (1032 nts, 696 nts). We observed that a major DI-RNA was detected for each rMV in the four different cell types (FIG. 1B).

Thus, we identified 5' copy-back DI-RNAs that were produced by rMVs. They differed in size for both loop and stem, but they all respected the so-called "rule of six" postulating that for the paramyxovirus subfamily Paramyxovirinae only hexameric-length genomes are replicated efficiently (32).

Example 9. Recombinant MVs that Express Heterologous Antigens are Efficient Producers of 5'Copy-Back DI Genomes First, we assessed if any perturbation of MV genome would outcome in production of DI genomes. Previous studies have demonstrated that rMVs expressing green fluorescent protein (GFP) or the Cherry red fluorescent protein (CH) gene from additional transcription unit on the viral genome were poor producers of DI genomes and behaved similar to the parental virus (15). We found a 402 nt-long DI-RNA in our viral stock of rMV-GFP and a 978 nt-long DI-RNA in our viral stock of rMV-CH (Table 2).

Figures 6A, 6B:
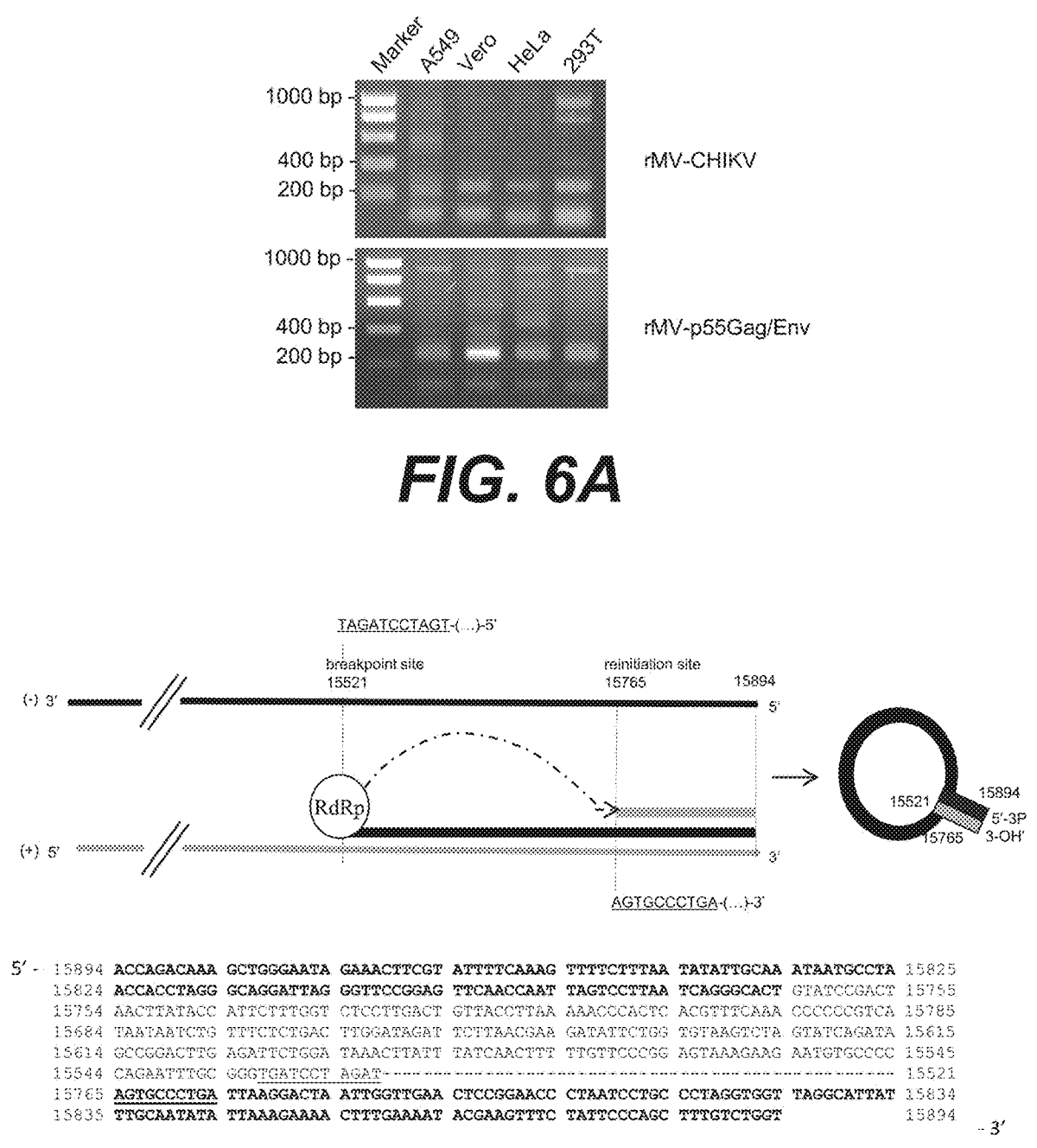

Further we examined whether or not recombinant MV-based vaccines expressing heterologous antigens could produce DI genomes. Vero, A549, 293T and HeLa cells were infected with either rMV-CHIKV expressing the structural proteins of Chikungunya virus (E1, E2, E3, C and 6K) (28) and rMV-p55Gag/Env expressing HIV-1 p55Gag polyprotein and EnvΔV1V2 envelope glycoprotein (29). As previously, total RNA was extracted and DI-RNAs were detected by RT-PCR using two DI genome specific primers (Table 1). We observed that upon infection both recombinant viruses produced 5' copy-back DI genomes (FIG. 6A). As above we performed their molecular characterization. rMV-CHIKV produced two different 5' copy-back DI genomes of 1260 nt- and 504 nt-long (Table 2, FIG. 6B). Interestingly rMV-dbp55Gag/Env produced two different DI RNAs of 1212 and 504 nt-long with the longest DI genome perfectly corresponding to the unique DI-RNA detected in cells infected with rMV-N. No insertions/deletions were found in any of the DI-RNAs in Table 2.

Therefore, we identify various 5' copy-back DI RNAs produced by rMVs that express heterologous genes. Again, these DI genomes all respected the "rule of six".

Example 10. Production of Various DI Genomes is an Intrinsic Quality of MV Infection To see whether DI genomes were dependent only on the type of genetic modification of the viral genome or on the rescue itself, we characterized DI genomes produced by two different stocks of either rMV-ΔC, or rMV-N, or rMV-CHIKV viruses obtained from two different rescues. We observed that the pattern of DI genomes was different for each rescue (Table 2, see rescues a and b). Indeed, previous studies have shown that DI-RNAs were produced very early after the rescue and this initial pattern defined the DI genome pattern of the viral stock (23). To be sure that these DI-RNAs were not due to the rescue system, we amplified a wt-MV from a patient sample in Vero/hSLAM cells permissive to the wt virus. We next infected Vero/hSLAM cells with the wt-MV at a MOI of 1 and assessed RT-PCR analysis for the presence of 5' copy-back DI genomes. Again, we identified the 1212 nt-long DI-RNA with identical breakpoint and re-initiation sites of the one produced by rMV-N and rMV-dbp55Gag/Env, but with differences in nucleotide sequence corresponding to the wt-MV (Measles virus genotype D4, Genbank accession number: KT732229).

These results validate that DI genomes production is an intrinsic quality of MV infection and that the same virus obtained from a different rescue can produce distinct 5' copy-back DI genomes.

Example 11. Some DI Genomes are Produced as Efficient as the Full-Length Genome

DI genomes are designated as defective interfering, as they are able to interfere with standard virus replication (33). In order to assess the question of interference, we quantified by RT-qPCR the full length and DI genomes produced by five different recombinant viruses: rMV-N, rMV-ΔV, rMV-ΔC, rMV-CHIKV, rMV-dbp55Gag/Env. Vero, A549, 293T and HeLa cells were infected at a MOI of 1 and total RNA purified from infected cells 24 hours post-infection. Absolute quantification was performed using serial dilutions of in vitro transcribed specific DI-RNAs or a MV full-length genome RNA fragment. MV-Schwarz, corresponding to an "empty of DI-RNA rMV", was used as a control. The absolute quantification of MV-Schwarz full-length genomes in the four different cell lines reached the same level of about $1 \cdot 10^8$ copy number of RNA molecules thus providing a "gold standard" for MV replication efficiency. We observed three different scenarii (FIG. 2): i) lack of the DI genome production (MV-Schwarz); ii) for some infection DI genomes production was as efficient as for the full-length genome (rMV-N and 2094 nt-long DI RNA of rMV-ΔC); iii) finally, some DI genomes were present in lower copy number compare to the higher level of the full-length genomes (rMV-ΔV, rMV-CHIKV and rMV-dbp55Gag/Env).

Further, the level of various DI genomes in each cell types was different. In most of the cases, Vero cells, that are interferon deficient cells (34), were more permissive to DI-RNAs production (FIG. 2). We failed to quantify some minor DI genomes by RT-qPCR (1032 nt-long DI-RNA of rMV-ΔC, 1260 nt-long DI-RNA of rMV-ΔV and rMV-CHIKV), probably due to their low level of production.

Thus, we observed that the ratio DI genome to the full-length MV genome varied greatly for the different rMVs.

Example 12. rMVs are Strong Inducers of the IFN Signalling Pathway in Cells

Figures 3A, 3B, 3C, 3D, 3E:
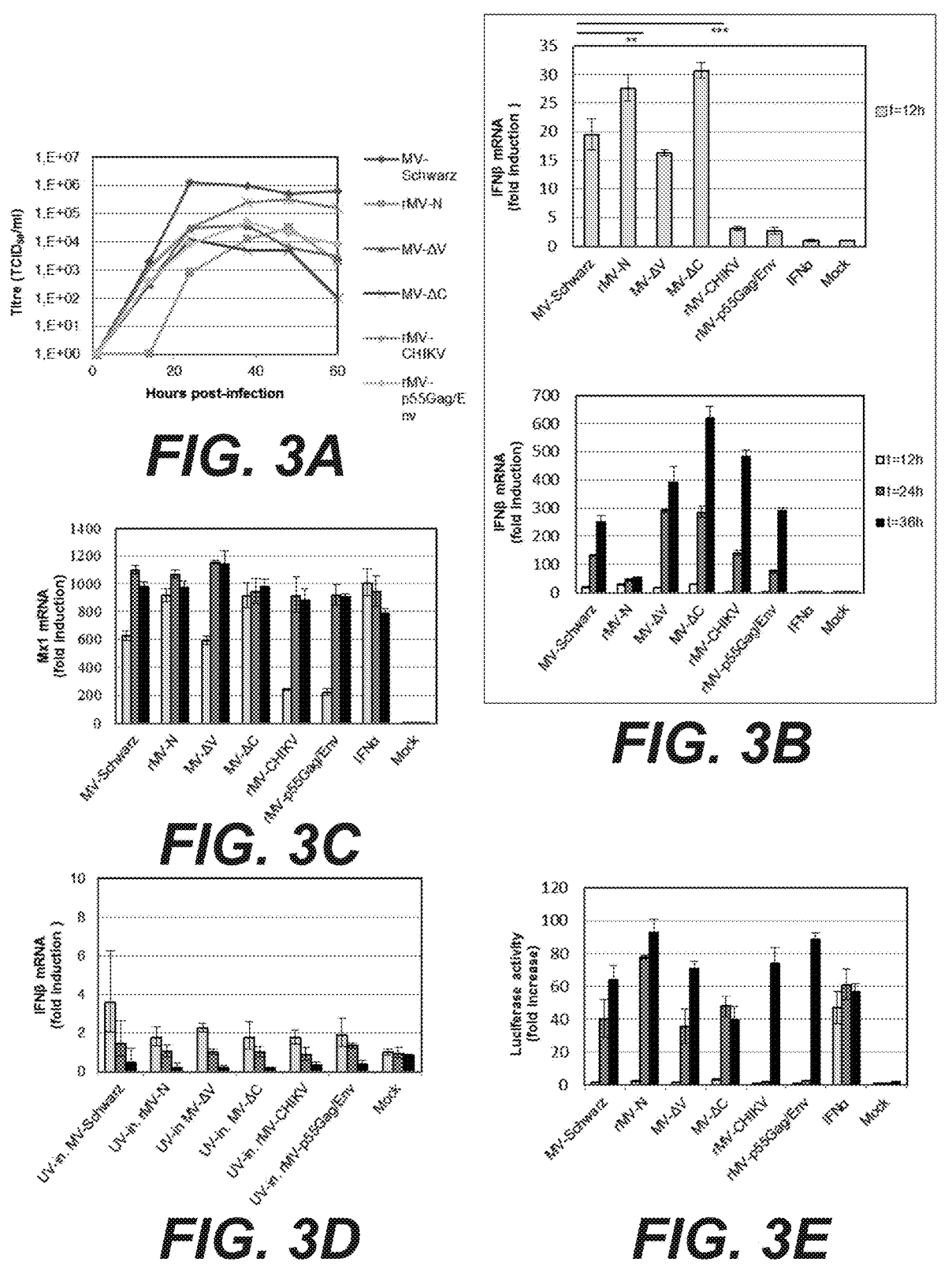

In the same experimental conditions we studied rMVs potential to induce type-I IFN signalling and compared it to the parental MV-Schwarz. First, we assessed the growth kinetics of MV-Schwarz, rMV-N, rMV-ΔV, rMV-ΔC, rMV-CHIKV and rMV-p55Gag/Env. A549 cells were infected with these five rMVs and the MV-Schwarz strain at a MOI of 1 and tittering was performed at six different time points. We observed that all rMVs grew slower than their parental MV-Schwarz, with a final titre varying from $1 \cdot 10^4$ to $1 \cdot 10^6$ $TCID_{50}$/ml (FIG. 3A). Then, we applied two different approaches to study immunostimulatory activity of these rMVs: (i) we measured rMV potential to induce IFN-β transcription and the transcription of Interferon Stimulated Gene (ISG) on A549 cells; (ii) we measured the type-I IFN stimulatory activity of rMVs at the protein level by using STING-37 cells that express an Interferon-Stimulated Response Element (ISRE)-luciferase reporter gene.

A549 cells were infected with corresponding rMVs and lysed at different time points (12 h, 24 h, 36 h) in order to quantify the IFN response (IFN-β and Mx1) by qRT-PCR gene expression assays (FIG. 3B-C). Level of IFN-β mRNA was higher for all of them except rMV-N (FIG. 3B). It is important to note that 36 hours post-infection, MV-Schwarz and rMV-CHIKV have almost reached the same titre (FIG. 3A), but rMV-CHIKV infected cells produced two fold more IFN-β mRNA than MV-Schwarz (FIG. 3B). Additionally, at the same time point, rMV-p55Gag/Env infected cells produced as many IFN-β mRNA as MV-Schwarz infected cells, whereas the titre of this virus was at least one log less high than the parental strain. Furthermore, we observed temporal differences in the IFN-β response: (i) rMV-N (t-test, p<0,05) and rMV-ΔC (t-test, p<0,001) that produced a high quantity of DI-RNAs, showed an early increase of IFN-β mRNA production at 12 hours post-infection (FIG. 7); (ii) rMV-ΔV and rMV-ΔC that lack the expression of virulence proteins presented higher level of IFN-β mRNA at 24 hours post-infection. Finally, the activation of ISG was achieved by all viruses as attested by the same level of induction of Mx1 mRNA production at 24 hours post-induction (FIG. 3C). Nevertheless, the level of Mx1 mRNA produced by infected cells early at 12 hours post-infection was higher for rMV-N (t-test, p<0,001) and rMV-ΔC (t-test, p<0,01).

To confirm the type-I IFN stimulatory activity of rMVs at the protein level, we used STING-37 cell line, corresponding to HEK-293 cells stably transfected with an ISRE-luciferase reporter gene (25). We validated that all rMVs including the backbone MV-Schwarz were strong IFN inducers in comparison to non-infected cells (FIG. 3D). Interestingly, for rMV-CHIKV and rMV-p55Gag/Env that are vaccine candidates, the ISRE activation by IFN-β was observed later, at 36 hours post-infection, but at a high level as for rMV-N and rMV-ΔV strains.

Thus, we linked presence of DI-RNAs with high immunostimulatory effects on type-I IFN signalling pathway, despite their negative impact on viral growth.

Figure 4B:
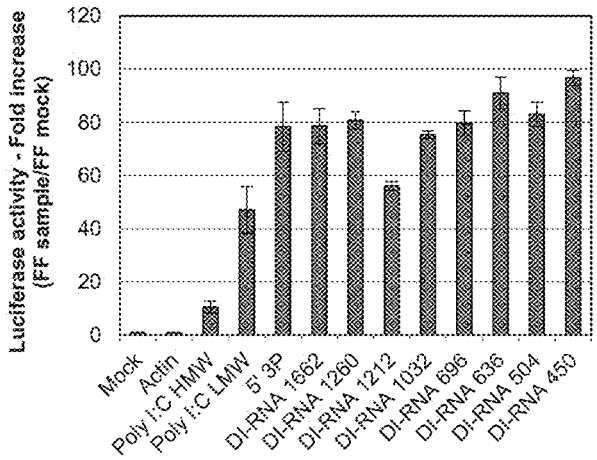
Figure 4C:
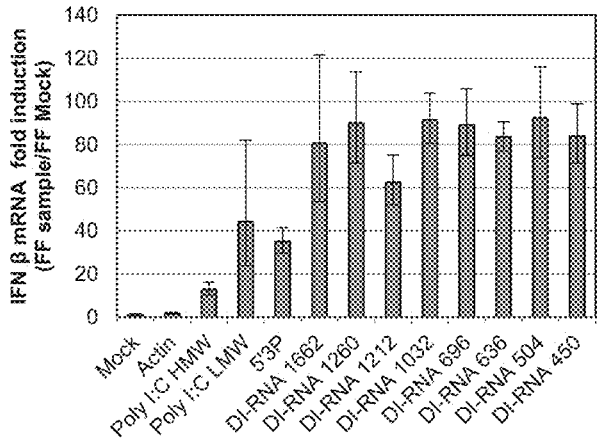

Example 13. Efficiency of Type-I IFN Signalling is Independent of DI-RNA Size or Sequence To compare type-I IFN activation potential of different DI-RNAs identified in this study (Table 2) we produced in vitro transcribed (IVT) DI-RNAs and transfected them in either STING-37 or A549 cells. We studied a total number of eight IVT DI-RNAs of different sizes and sequences: 1662, 1260, 1212, 1032, 696, 636, 504 and 450 nt-long DI-RNAs (FIG. 4A and Table 2). β-actin RNA was used as negative control, and three classical RLRs PAMPs were used as positive control: poly I:C of high molecular weight (HMW) or low molecular weight (LMW) and 5′ triphosphate RNA (5′3P). IFN transcription efficiency was assessed in A549 cells by qRT-PCR and type-I IFN protein level potential was observed using the ISRE-luciferase reporter assay (FIG. 4B,C and FIG. 8). We observed that our eight DI-RNAs efficiently activated the type-I interferon pathway with little difference between DI-RNAs for two approaches applied (FIG. 4B-C).

Thus, we showed that type-I IFN activation was achieved by all IVT DI-RNA, independently of their size or sequence.

Example 14. MV 5′ Copy-Back DI-RNAs are Specific Agonists of RIG-I and LGP2, but not MDA5

To test if each of the three RLRs are involved in DI genome sensing and to compare LGP2, MDA-5 and RIG-I efficiency in binding various 5′ copy-back DI genomes we used human HEK293 cell lines stably expressing tagged LGP2, or MDA5 or RIG-I proteins (assigned ST-RLRs (13)). These cells have been shown to be efficient and specific tool to purify viral agonists of RLR. ST-RLRs cells were infected with MV-Schwarz, rMV-ΔV, rMV-ΔC and rMV-CHIKV for 24 hours at a MOI of 1. RLR-specific RNA ligands were purified using previously published protocol (13). In addition, a stable cell line (assigned ST-CH) expressing the Cherry protein instead of tagged RLRs was used as a negative control to allow subtraction of non-specific RNA binding (13). The efficacy of the purification was assessed by western blot to confirm the enrichment of RLRs receptors and the depletion of β-actin (FIG. 8). Absolute quantification of DI-RNA, genomes and β-actin mRNA was done by qRT-PCR. Ratios of the full-length genomes to actin and DI-RNAs to actin showed that DI-RNAs were always enriched on RIG-I, to a lesser extent on LGP2 and never on MDA5 (FIG. 5). Full-length genome was equally depleted on the three RLRs for MV-Schwarz and any of the rMV infections.

Therefore, we validated that various DI-RNAs specifically interact with RIG-I and for the first time observed their binding to LGP2.

Example 15. The Capacity of MV DI-RNA to Activate Type-I IFN Response is Lost when DI-RNA is Encapsidated into MV Nucleocapsid Material and Method:

[98] HEK293-T7 and HEK293-T7-NP cells express the T7 RNA polymerase in the cytosol. HEK-293-T7-NP cells also stably express MV-N and MV-P proteins necessary for MV genome encapsidation. Both cells were transfected by p2RZ plasmids expressing different MV DI-RNAs. After 24 hours total RNA was extracted using the RNeasy Mini Kit and treated by RQ1 RNase-Free DNase (#M6101, Promega). Expression levels of IFN-β or Mx1 and DHX58 interferon stimulated genes (ISG) were quantified by one-step real-time PCR using GAPDH mRNA expression as internal control. RNA (100 ng) was amplified with 20× custom TaqMan Gene Expression Assays (IFN-β #Hs01077958_s1; Mx1 #Hs00895608_m1; DHX58

Hs00225561_m1; GAPDH #Hs99999905_m1, Life Technologies) using TaqMan RNA-to-Ctl-Step Kit in accordance with the manufacturer's instructions. All measurements were performed in triplicate and analysed as generated by StepOnePlus™ software system.

Results:

To investigate whether MV DI-RNAs encapsidated within MV nucleocapsids were as efficient as non-encapsidated ones to stimulate type-I IFN, we used HEK293-T7 and HEK293-T7-NP cell lines that both stably express T7 RNA Polymerase but only HEK293-T7-NP cells also produce MV-N and P proteins (A). HEK293-T7 and HEK293-T7-NP cells were transfected with p2RZ vectors expressing 1212 nt-long DI-RNA (p2RZ-DI1212), 450 nt-long DI-RNA (p2RZ-DI450), 1260 nt-long DI-RNA (p2RZ-DI1260) or a 1212 nt-long RNA fragment of actin mRNA (p2RZ-actin). The p2RZ plasmid allows producing RNA transcripts under the control of T7 Polymerase promoter and possesses 3'-end cis-acting ribozyme of hepatitis delta virus (HDV) for direct transcriptional processing to precisely trim the RNA transcript 3'-end.

Upon transfection of p2RZ-DI1212, p2RZ-DI450 and p2RZ-DI1260 vectors both cell lines produced a similar amount of DI-RNA (B). However, only HEK293-T7 showed a significant increased level of IFN-$\beta$ while HEK293-T7-NP cells did not. As expected, no type-I IFN activation was observed in both cell lines upon transfection with the negative control p2RZ-actin vector (C). Furthermore, we analysed the potential of DI-RNAs to stimulate type-I IFN by transfecting in vitro transcribed (IVT) DI-RNAs in HEK293-T7 and HEK293-T7-NP cells (D). As above, HEK293-T7-NP cells presented a lower type-I IFN activation than HEK293-T7 cells upon transfection of the IVT DI-RNAs, whereas control stimulation by 5'3P RNA was identical in the two cell lines. In that case, the presence of MV N and P in HEK293-T7-NP cells decreased type-I IFN activation by DI genomes but did not abrogate it. Importantly, we observed similar type-I IFN activation by plasmid-derived or in vitro transcribed DI-RNAs in HEK293-T7 cells, whereas in HEK293-T7-NP cells the plasmid-derived DI genomes were less potent. This indicates that the rapid encapsidation immediately after RNA synthesis from p2RZ-DI-RNA vectors in HEK293-T7-NP cells masked viral RNA and abolished its recognition and downstream activation of type-I IFN signalling.

Conclusion:

These results show that encapsidation of DI-RNA by MV-N and MV-P proteins abolished its capacity to stimulate type-I IFN. This demonstrates that naked DI-RNA is the molecular form that is recognized by RLRs to activate type-I IFN

Example 16. Administration of an MV-Derived Virus as an Adjuvant

Viruses and Antigens

MV-Schwarz and rMV-CHIKV design and production have been described previously (Combredet, J Virol, 2003; Brandler, Vaccine, 2013). Recombinant circumsporozoite proteins from *Plasmodium falciparum* (CSPf) were produced in *E. coli* (Malaria Parasite Biology and Vaccines Unit, Institut Pasteur, Paris). Alum was used as positive control to enhance immunogenicity of the CSPf.

Study Design

C57Bl/6 mice were obtained from Charles River Laboratory, with an average age of 5 weeks. Four Groups of 6 mice were inoculated intraperitoneally (i.p.) with 5 µg of CSPf alone, 5 µg of CSPf+$10^5$ TCID$_{50}$ of rMV-CHIKV, or 5 µg of CSPf+Alum. A second immunization was performed 4 weeks later, with the same dose and route of delivering. For antibody determination, blood samples were collected at day 0 (negative control), day 28 (before the boost) and at day 55 (4 weeks after the boost). All experiments were approved and conducted in accordance with the guidelines of the Office of Laboratory Animal Care at Pasteur Institute.

Humoral Response

The presence of anti-CS antibodies was assessed using enzyme-linked immunosorbent assay (ELISA). 96-well plates were coated with recombinant CS protein diluted in carbonate buffer at a concentration of 1 µg/ml. The plates were incubated overnight at +4° C. and washed with PBS-0.05% Tween 20. Unspecific interactions were blocked with 3% BSA in PBS for 1 hour at 37° C. After washing, plates were incubated with serial dilutions of mouse sera for 1 hour at 37° C. Horse-radish peroxidase-conjugated goat anti-mouse IgG was used as secondary antibody and plates were revealed using TMB substrate. The endpoint titers for each individual serum were calculated as the reciprocal of the last dilution giving twice the absorbance of negative control sera.

Results:

The recombinant CS protein was used as a model antigen. The CS alone is immunogenic and induced an antibody response, which was weakly boosted after the second immunization. The addition of rMV-CHIKV or Alum (positive control group) enhanced the antibody response. After the second immunization, we observed ten times higher level of antibodies in the group immunized with CS together with rMV-CHIKV compared to the group immunized with CS alone, highlighting the adjuvant effect of the virus to the recombinant protein.

Conclusion:

rMV-CHIKV has an adjuvant effect in mice in vivo when added to a recombinant protein. This observation allows adding recombinant antigens to the viral vector to benefit of a natural adjuvant effect.

Example 17. Capacity of MV-Schwarz to Encapsidate a Transfected RNA and to Maintain it in the New Viral Stock Material and Method:

T25 flasks of HEK293T cells were transfected with 1 µg of IVT-DI-RNA-450 or were mock-transfected using Jet-Prime® polyplus transfection reagent. Seven hours later, cells were infected with either MV-Schwarz or rMV-N at a MOI of 1. Infections were stopped after 24 hours in 500 µl of Optimem® and frozen at −80° C. After thawing, 250 µl of the new virus stocks were used to infect T25 flasks of Vero cells. Two hours after infection, supernatants were removed and DMEM was added in each flask. Infections were stopped by cell lysis after removing the supernatant 48 hours later, and total RNA was extracted with RNeasy mini kit. Then, genome and DI-RNA were detected by RT-PCR (see above).

Results:

Measles genome was detected in each case, confirming that all new viral stocks were able to infect and disseminate in Vero cells (the presence of syncytia was also assessed by microscopy). 450 nt-long DI-RNA was detected in Vero cells infected with the new MV-Schwarz viral stock, confirming that this RNA was delivered into the cells via the viral particles. The same was observed with rMV-N that still delivered its 1212 nt-long DI-RNA but that also delivered the new 450 nt-long DI-RNA to the cells via the viral particles.

Conclusion:

MV-Schwarz or rMV are able to encapsidate a transfected RNA and to maintain it in the new viral stock so that we can detect it in new infected cells. These results highlighted two important points: (i) it is possible to control the presence of a defined DI-RNA in a MV-Schwarz viral stock; (ii) MV-Schwarz could potentially encapsidate any RNA that would respect the rule of six necessary for its encapsidation and deliver said RNA to cells.

Example 18. Testing the Adjuvant Effect of MV Expressing DI-RNA in Human Dendritic Cells Material and Method:

Human myeloid dendritic cells (MoDCs) were used to analyse the presentation of HIV-1 Gag epitopes to HIV-1 Gag-specific CD4+ T cells. Obtained from HLA-DRb1*01+ CD14+monocytes incubated with IL-4 and GM-CSF during 4 days, DCs were exposed to recombinant Gagp24 protein at different concentrations (2 µg and 10 µg) alone, or with MV-Schwarz, or MV-Schwarz p8 at a MOI of 0.5 or 5. After 2 hours of incubation in RPMI at 37° C., 5% CO2, cells were washed and incubated in 24-well plates at 37° C., 5% CO2 for 24 hours. HIV-1-Gag specific CD4+ T cells (clone F12) were added at a ratio of 1:40. As a positive control, DCs previously incubated with HIV-1 peptides (SL9 and gag2) or with rMV-p55Gag/Env were also incubated with T cell clones at the same ratio. After 6 hours of coculture, the activation of CD4+ T cells was measured by intracellular cytokine staining (anti-MIP-1B and a pool of anti-IL-2, -IFNg and -TNFa conjugated to the same fluorochrome) using flow cytometry. Schwarz p8 was obtained after 8 passages of MV-Schwarz on Vero cells at a MOI of 0.1. The genome sequences of both viruses are identical but Schwarz p8 viral stock contains DI-RNA whereas MV-Schwarz does not.

Results:

DCs that are exposed simultaneously to recombinant Gagp24 antigen and Schwarz p8 activated a higher percentage of anti-Gagp24 CD4+ T cells than DCs exposed to recombinant protein alone or with MV-Schwarz. Moreover, these T cells clones presented higher polyfunctionality by the co-expression of MIP-1B, IL-2, IFNg and TNFa. Nevertheless, the effect was weak and lost at a higher MOI. Indeed, the clonal system is highly sensitive and rapidly reached a plateau of activation Conclusion:

Schwarz p8 that is similar to MV-Schwarz in the sequence but only differs by the presence of DI-RNA is able to enhance DCs and T cell activation exposed to recombinant Gagp24 antigen. These results are consistent with the already known capacity of DI-RNA to induce a greater maturation of moDCs and higher levels of IFN and ISGs (Shivakoti R, 2013, J Virol), and emphasize the adjuvant role of DI-RNA in a viral stock.

Example 19. Discussion

DI-RNAs were known to be produced by some modified MV (rMV-N (10), rMV-ΔV (13), rMV-ΔC (23)), or by some measles vaccine strains after cell passages at a high MOI (8,20,22). By comparing different stocks of rMVs produced by the same manner, we observed that any modification of the MV genome increased its capacity to produce DI-RNAs. Indeed, no DI-RNA was found in the parental MV-Schwarz stock, whereas all rMVs tested produced one or more DI-RNAs. This includes addition of genetic material (rMV-GFP, rMV-CH, rMV-N, rMV-CHIKV, rMVp55Gag/Env) or lacking of the expression of virulence factors, C and V protein (rMV-ΔC or rMV-ΔV). Both proteins have at least two functions: modulation of the innate immune response (35-37) and regulation of viral RNA synthesis. C protein is described as an important factor that stabilizes the RNP-polymerase complex, as a lack of C protein results in more frequent chain termination occurring both during transcription and replication (15). And V protein helps maintaining the ratio of genome to antigenome synthesis during replication (38). But the exact mechanism used by the polymerase to stop the replication and start copying back remains unknown. Moreover, the pattern of DI-RNA is different for each viral stock and multiple breakpoint sites and initiation sites were identified, especially for rMV-ΔC. This pattern is defined early after the rescue, as showed by Pfaller et al. (23). Nevertheless, we found 1212 nt-long DI-RNA in three different viral stocks (rMV-N, rMV-P55Gag/Env, and wt-MV), suggesting that the polymerase may recognize some specific nucleotide sequences.

DI-RNAs length ranged from 402 nt to 2094 bp. The loop and stem sizes varied from one DI-RNA to another, but interestingly all identified sequences respected the "rule of six" that is necessary for encapsidation efficiency (21,23, 32). The minimal size of the double stranded stem region, 93 nt, included the B' box of the trailer sequence (39). This is also the minimal size observed by Pfaller et al (23) and is comparable to the minimal length of 96 nt observed in Sendai Virus copy-back DI-RNAs, an other paramyxovirus (40). This minimal sequence is necessary for genome encapsidation by N and P proteins (41,42). MV genome is encapsidated immediately after the beginning of the replication (4) and the rule of six necessary for encapsidation (32) may have advantaged the replication and transmission from cell to cell of DI-RNAs respecting this rule. However, Pfaller et al. found naked dsRNA in cells infected by rMV-ΔC (15), as well as DI-RNA with a length that does not respect this rule (23). As C protein stabilized the polymerase complex, its absence might enhance a higher production of DI-RNAs that overpasses the fitness of encapsidation.

Defective viral genomes are named as defective "interfering" RNA because DI-RNA particles were postulated to interfere with the replication of the standard virus by competing for viral proteins in the infected cell (43). In our study, all rMVs have a decreased growth compared to MV-Schwarz, meaning that the genetic modifications have a cost for viral fitness. The slowest growths were observed for rMV-N and rMV-ΔC that both produced as many DI-RNAs as genomes. These DI-RNAs may indeed decrease viral growth by interfering directly with the viral replication but also by enhancing the host response due to their presence in high quantity as PAMPs recognized by the innate immune system.

5' copy back DI-RNAs are known to be PAMPs to RLR-intracellular receptors, specifically RIG-I (12,44) but also MDA5 (45). We showed a direct interaction between DI-RNAs and RIG-I and LGP2 by infecting ST-RLR cell lines (13). These cells enabled isolation of RLR interactors by using chromatographic affinity purification. DI-RNAs were amplified in RNAs associated with RIG-I and LGP2 receptors and not MDA5. We described for the first time an interaction between LGP2 and DI-RNA. LGP2 differed from RIG-I and MDA5 by the absence of CARD domain that is necessary to activate the final common IFN signalling cascade via MAVS activation (46). The role of LGP2 as a regulator of MDA5 and RIG-I response is not well understood and controversial. It acts mainly as a negative regulator of RIG-I (47) and a positive regulator of MDA5 (48-50). Common ligands between MDA5 and LGP2 are suggested (13,51) and MDA5 may play a role in the induction of an antiviral state in cells infected by measles vaccine by recognizing others PAMPs of MV than DI-RNA (13,52). Here, we described DI-RNA as a common ligand between RIG-I and LGP2. As all rMVs shared high immunostimulatory properties on IFN and ISG expression, both regulatory functions of LGP2 could be involved: enhancement of RIG-I response, or down-regulation to avoid excessive response, but that still permit a high activation.

DI-RNAs sequences were highly preserved with no mutation observed for all DI-RNAs, except 1032 nt-long DI-RNA. This DI-RNA produced by rMV-ΔC virus accumulated clusters of A-to-G transitions. This pattern was already observed by Pfaller et al (23) for DI-RNAs produced by Moraten vaccine strain and wild-type IC-B strain lacking expression of C-protein. ADAR1-editing was hypothesized to destabilize unencapsidated DI-RNAs that have dsRNA structures (23). But in our case, A-to-G transitions, observed in 36 upon 286 A nucleotides (12.7%), were located in the loop sequence only. These mutations did not affect its immunostimulatory properties, as the general structure is conserved. Indeed, cells transfected with eight in vitro transcribed DI-RNAs different in sizes and sequences showed similar high level of IFN 13 and ISG expression on STING-37 and A549 cells. These experiments confirmed that the PAMP recognized by RIG-I and LGP2 is structure dependent and do not depend on the sequence or the size of ssRNA loop and dsRNA stem. Moreover, Ho et al (14) also confirmed that the 5'3P extremity play a major role for the recognition by RIG-I.

MV vaccine strains are stronger inducers of IFN pathway compared to wt-MV (20), even in the absence of DI-RNA. Here, we showed that all rMVs tested possessed higher immunostimulatory properties than the parental strain MV-Schwarz due to the production of DI-RNAs. These specific viral PAMPs are bound to RIG-I and LGP2, both cytosolic receptors of the innate immunity. Measles-virus-based vaccine platform is of great interest since rMV-CHIKV vaccine have shown in a phase I clinical trial that pre-immunity against measles did not interfere with the induction of an immunogenicity against heterologous antigens expressed by the vector (24). Efficiency of vaccines depends on their immunostimulatory properties. 5' copy-back DI-RNAs act as intrinsic adjuvants naturally produced by measles vector, as they enhance recognition and activation of the innate immune system. They certainly play a major role in MV efficiency as a vector against heterologous antigens and their presence should be considered of great importance.

REFERENCES

1. Lazzarini, R. A., Keene, J. D. and Schubert, M. (1981) The origins of defective interfering particles of the negative-strand RNA viruses. *Cell*, 26, 145-154.
2. Dimmock, N. J. and Easton, A. J. (2014) Defective interfering influenza virus RNAs: time to reevaluate their clinical potential as broad-spectrum antivirals? *Journal of virology*, 88, 5217-5227.
3. Lopez, C. B. (2014) Defective viral genomes: critical danger signals of viral infections. *Journal of virology*, 88, 8720-8723.
4. Gubbay, O., Curran, J. and Kolakofsky, D. (2001) Sendai virus genome synthesis and assembly are coupled: a possible mechanism to promote viral RNA polymerase processivity. *The Journal of general virology*, 82, 2895-2903.
5. Bellini, W. J., Englund, G., Rozenblatt, S., Arnheiter, H. and Richardson, C. D. (1985) Measles virus P gene codes for two proteins. *Journal of virology*, 53, 908-919.
6. Cattaneo, R., Kaelin, K., Baczko, K. and Billeter, M. A. (1989) Measles virus editing provides an additional cysteine-rich protein. *Cell*, 56, 759-764.
7. Strahle, L., Garcin, D. and Kolakofsky, D. (2006) Sendai virus defective-interfering genomes and the activation of interferon-beta. *Virology*, 351, 101-111.
8. Shingai, M., Ebihara, T., Begum, N. A., Kato, A., Honma, T, Matsumoto, K., Saito, H., Ogura, H., Matsumoto, M. and Seya, T. (2007) Differential type I IFN-inducing abilities of wild-type versus vaccine strains of measles virus. *Journal of immunology*, 179, 6123-6133.
9. Mercado-Lopez, X., Cotter, C. R., Kim, W. K., Sun, Y., Munoz, L., Tapia, K. and Lopez, C. B. (2013) Highly immunostimulatory RNA derived from a Sendai virus defective viral genome. *Vaccine*, 31, 5713-5721.
10. Komarova, A. V., Combredet, C., Sismeiro, O., Dillies, M. A., Jagla, B., Sanchez David, R. Y., Vabret, N., Coppee, J. Y., Vidalain, P. O. and Tangy, F. (2013) Identification of RNA partners of viral proteins in infected cells. *RNA biology*, 10, 944-956.
11. Baum, A., Sachidanandam, R and Garcia-Sastre, A. (2010) Preference of RIG-I for short viral RNA molecules in infected cells revealed by next-generation sequencing. *Proceedings of the National Academy of Sciences of the United States of America*, 107, 16303-16308.
12. Runge, S., Sparrer, K. M., Lassig, C., Hembach, K., Baum, A., Garcia-Sastre, A., Soding, J., Conzelmann, K. K. and Hopfner, K. P. (2014) In vivo ligands of MDA5 and RIG-I in measles virus-infected cells. *PLoS pathogens*, 10, e1004081.
13. Sanchez David, R. Y., Combredet, C., Sismeiro, O., Dillies, M. A., Jagla, B., Coppee, J. Y., Mura, M., Guerbois Galla, M., Despres, P., Tangy, F. et al. (2016) Comparative analysis of viral RNA signatures on different RIG-I-like receptors. *eLife*, 5.
14. Ho, T. H., Kew, C., Lui, P. Y., Chan, C. P., Satoh, T., Akira, S., Jin, D. Y. and Kok, K. H. (2015) PACT- and RIG-I-Dependent Activation of Type I Interferon Production by a Defective Interfering RNA Derived from Measles Virus Vaccine. *Journal of virology*, 90, 1557-1568.
15. Pfaller, C. K., Radeke, M. J., Cattaneo, R. and Samuel, C. E. (2014) Measles virus C protein impairs production of defective copyback double-stranded viral RNA and activation of protein kinase R. *Journal of virology*, 88, 456-468.
16. Saira, K., Lin, X., DePasse, J. V., Halpin, R., Twaddle, A., Stockwell, T., Angus, B., Cozzi-Lepri, A., Delfino, M., Dugan, V. et al. (2013) Sequence analysis of in vivo defective interfering-like RNA of influenza A H1N1 pandemic virus. *Journal of virology*, 87, 8064-8074.
17. Li, D., Lott, W. B., Lowry, K., Jones, A., Thu, H. M. and Aaskov, J. (2011) Defective interfering viral particles in acute dengue infections. *PLoS one*, 6, e19447.
18. Prince, A. M., Huima-Byron, T., Parker, T. S. and Levine, D. M. (1996) Visualization of hepatitis C virions and putative defective interfering particles isolated from low-density lipoproteins. *Journal of viral hepatitis*, 3, 11-17.

19. Sun, Y., Jain, D., Koziol-White, C. J., Genoyer, E., Gilbert, M., Tapia, K., Panettieri, R. A., Jr., Hodinka, R. L. and Lopez, C. B. (2015) Immunostimulatory Defective Viral Genomes from Respiratory Syncytial Virus Promote a Strong Innate Antiviral Response during Infection in Mice and Humans *PLoS* pathogens, 11, e1005122.

20. Kessler, J. R., Kremer, J. R. and Muller, C. P. (2011) Interplay of measles virus with early induced cytokines reveals different wild type phenotypes. *Virus research*, 155, 195-202.

21. Calain, P and Roux, L. (1988) Generation of measles virus defective interfering particles and their presence in a preparation of attenuated live-virus vaccine. *Journal of virology*, 62, 2859-2866.

22. Whistler, T., Bellini, W. J. and Rota, P. A. (1996) Generation of defective interfering particles by two vaccine strains of measles virus. *Virology*, 220, 480-484.

23. Pfaller, C. K., Mastorakos, G. M., Matchett, W. E., Ma, X., Samuel, C. E. and Cattaneo, R. (2015) Measles Virus Defective Interfering RNAs Are Generated Frequently and Early in the Absence of C Protein and Can Be Destabilized by Adenosine Deaminase Acting on RNA-1-Like Hypermutations. *Journal of virology*, 89, 7735-7747.

24. Ramsauer, K., Schwameis, M., Firbas, C., Mullner, M., Putnak, R. J., Thomas, S. J., Despres, P., Tauber, E., Jilma, B and Tangy, F. (2015) Immunogenicity, safety, and tolerability of a recombinant measles-virus-based chikungunya vaccine: a randomised, double-blind, placebo-controlled, active-comparator, first-in-man trial. *The Lancet. Infectious diseases*, 15, 519-527.

25. Lucas-Hourani, M., Munier-Lehmann, H., Helynck, O., Komarova, A., Despres, P., Tangy, F. and Vidalain, P. O. (2014) High-throughput screening for broad-spectrum chemical inhibitors of RNA viruses. *Journal of visualized experiments: JoVE*.

26. Combredet, C., Labrousse, V., Mollet, L., Lorin, C., Delebecque, F., Hurtrel, B., McClure, H., Feinberg, M. B., Brahic, M. and Tangy, F. (2003) A molecularly cloned Schwarz strain of measles virus vaccine induces strong immune responses in macaques and transgenic mice. *Journal of virology*, 77, 11546-11554.

27. Richetta, C., Gregoire, I. P., Verlhac, P., Azocar, O., Baguet, J., Flacher, M., Tangy, F., Rabourdin-Combe, C. and Faure, M. (2013) Sustained autophagy contributes to measles virus infectivity. *PLoS* pathogens, 9, e1003599.

28. Brandler, S., Ruffle, C., Combredet, C., Brault, J. B., Najburg, V., Prevost, M. C., Habel, A., Tauber, E., Despres, P. and Tangy, F. (2013) A recombinant measles vaccine expressing chikungunya virus-like particles is strongly immunogenic and protects mice from lethal challenge with chikungunya virus. *Vaccine*, 31, 3718-3725.

29. Guerbois, M., Moris, A., Combredet, C., Najburg, V., Ruffle, C., Fevrier, M., Cayet, N., Brandler, S., Schwartz, O. and Tangy, F. (2009) Live attenuated measles vaccine expressing HIV-1 Gag virus like particles covered with gp160DeltaV1V2 is strongly immunogenic. *Virology*, 388, 191-203.

30. Radecke, F., Spielhofer, P., Schneider, H., Kaelin, K., Huber, M., Dotsch, C., Christiansen, G. and Billeter, M. A. (1995) Rescue of measles viruses from cloned DNA. *The EMBO journal*, 14, 5773-5784.

31. Parks, C. L., Lerch, R. A., Walpita, P., Sidhu, M. S. and Udem, S. A. (1999) Enhanced measles virus cDNA rescue and gene expression after heat shock. *Journal of virology*, 73, 3560-3566.

32. Kolakofsky, D., Roux, L., Garcin, D. and Ruigrok, R. W. (2005) Paramyxovirus mRNA editing, the "rule of six" and error catastrophe: a hypothesis. *The Journal of general virology*, 86, 1869-1877.

33. Pathak, K. B. and Nagy, P. D. (2009) Defective Interfering RNAs: Foes of Viruses and Friends of Virologists. *Viruses*, 1, 895-919.

34. Desmyter, J., Melnick, J. L. and Rawls, W. E. (1968) Defectiveness of interferon production and of rubella virus interference in a line of African green monkey kidney cells (Vero). *Journal of virology*, 2, 955-961.

35. Caignard, G., Guerbois, M., Labernardiere, J. L., Jacob, Y., Jones, L. M., Infectious Mapping Project, I. M., Wild, F., Tangy, F. and Vidalain, P. O. (2007) Measles virus V protein blocks Jakl-mediated phosphorylation of STAT1 to escape IFN-alpha/beta signaling. *Virology*, 368, 351-362.

36. Irie, T., Kiyotani, K., Igarashi, T., Yoshida, A. and Sakaguchi, T. (2012) Inhibition of interferon regulatory factor 3 activation by paramyxovirus V protein. *Journal of virology*, 86, 7136-7145.

37. Sparrer, K. M., Pfaller, C. K. and Conzelmann, K K (2012) Measles virus C protein interferes with Beta interferon transcription in the nucleus. *Journal of virology*, 86, 796-805.

38. Parks, C. L., Witko, S. E., Kotash, C., Lin, S. L., Sidhu, M. S. and Udem, S. A. (2006) Role of V protein RNA binding in inhibition of measles virus minigenome replication. *Virology*, 348, 96-106.

39. Parks, C. L., Lerch, R. A., Walpita, P., Wang, H. P., Sidhu, M. S. and Udem, S. A. (2001) Analysis of the noncoding regions of measles virus strains in the Edmonston vaccine lineage. *Journal of virology*, 75, 921-933.

40. Salinas, Y. and Roux, L. (2005) Replication and packaging properties of short Paramyxovirus defective RNAs. *Virus research*, 109, 125-132.

41. Bhella, D., Ralph, A. and Yeo, R. P. (2004) Conformational flexibility in recombinant measles virus nucleocapsids visualised by cryo-negative stain electron microscopy and real-space helical reconstruction. *J Mol Biol*, 340, 319-331.

42. Tapparel, C., Maurice, D. and Roux, L. (1998) The activity of Sendai virus genomic and antigenomic promoters requires a second element past the leader template regions: a motif (GNNNNN)3 is essential for replication. *Journal of virology*, 72, 3117-3128.

43. Perrault, J. (1981) Origin and replication of defective interfering particles. *Current topics in microbiology and immunology*, 93, 151-207.

44. Martinez-Gil, L., Goff, P. H., Hai, R., Garcia-Sastre, A., Shaw, M. L. and Palese, P. (2013) A Sendai virus-derived RNA agonist of RIG-I as a virus vaccine adjuvant. *Journal of virology*, 87, 1290-1300.

45. Yount, J. S., Gitlin, L., Moran, T. M. and Lopez, C. B. (2008) MDA5 participates in the detection of paramyxovirus infection and is essential for the early activation of dendritic cells in response to Sendai Virus defective interfering particles. *Journal of immunology*, 180, 4910-4918.

46. Yoneyama, M., Kikuchi, M., Matsumoto, K., Imaizumi, T, Miyagishi, M., Taira, K., Foy, E., Loo, Y. M., Gale, M., Jr., Akira, S. et al. (2005) Shared and unique functions of the DExD/H-box helicases RIG-I, MDA5, and LGP2 in antiviral innate immunity. *Journal of immunology*, 175, 2851-2858.

47. Rothenfusser, S., Goutagny, N., DiPerna, G., Gong, M., Monks, B. G., Schoenemeyer, A., Yamamoto, M., Akira, S. and Fitzgerald, K. A. (2005) The RNA helicase Lgp2 inhibits TLR-independent sensing of viral replication by retinoic acid-inducible gene-I. *Journal of immunology,* 175, 5260-5268.
48. Rodriguez, K. R., Bruns, A. M. and Horvath, C. M. (2014) MDA5 and LGP2: accomplices and antagonists of antiviral signal transduction. *Journal of virology,* 88, 8194-8200.
49. Parisien, J. P., Bamming, D., Komuro, A., Ramachandran, A, Rodriguez, J. J., Barber, G., Wojahn, R. D. and Horvath, C. M. (2009) A shared interface mediates paramyxovirus interference with antiviral RNA helicases MDA5 and LGP2. *Journal of virology,* 83, 7252-7260.
50. Childs, K. S., Randall, R E and Goodbourn, S. (2013) LGP2 plays a critical role in sensitizing mda-5 to activation by double-stranded RNA. *PloS one,* 8, e64202.
51. Bruns, A. M., Leser, G. P., Lamb, R. A. and Horvath, C. M. (2014) The innate immune sensor LGP2 activates antiviral signaling by regulating MDA5-RNA interaction and filament assembly. *Mol Cell,* 55, 771-781.
52. Berghall, H., Siren, J., Sarkar, D., Julkunen, I., Fisher, P. B., Vainionpaa, R. and Matikainen, S. (2006) The interferon-inducible RNA helicase, mda-5, is involved in measles virus-induced expression of antiviral cytokines. *Microbes Infect,* 8, 2138-2144.

---

The invention claimed is:

1. A composition of products comprising:

a mixture of particles of a rescued recombinant Measles virus (MV) encoding at least one antigen (the "vectored antigen") or of a rescued modified recombinant MV lacking expression of virulence factors and encoding at least one antigen (the "vectored antigen"), said mixture comprising infectious replicating viral particles and defective interfering (DI) particles; and a protein antigen.

2. A composition of products comprising:

a mixture of particles of a rescued recombinant MV encoding at least one antigen (the "vectored antigen") or of a rescued modified recombinant MV lacking expression of virulence factors and encoding at least one antigen (the "vectored antigen"), said mixture comprising infectious replicating viral particles and a defective interfering (DI) genome as DI-RNA in RNA form; and a protein antigen.

3. The composition of claim 1, wherein the rescued recombinant MV particles encode at least one antigen which is not from MV.

4. The composition of claim 1, wherein the vectored antigen and the protein antigen are from at least two distinct infectious species, in particular from two distinct viruses.

5. The composition of claim 1, wherein the vectored antigen and the protein antigen are the same, or wherein at least one vectored antigen is the same as at least one protein antigen.

6. The composition of claim 1, wherein the DI genomes (i.e. the genomes of the DI particles) represent at least 0.00001% of the full-length MV genomic RNA in the composition.

7. The composition of claim 1, wherein at least one vectored antigen and/or protein antigen is from an arbovirus.

8. The composition of claim 7, wherein the arbovirus is selected from the group consisting of Chikungunya Virus (CHIKV), Dengue Virus (DV), West-Nile Virus (WNV), Yellow Fever Virus (YFV), and ZIKA virus (ZV).

9. The composition of claim 1, wherein the at least one vectored antigen and/or protein antigen is from *Plasmodium falciparum*.

10. The composition of claim 7, wherein the vectored antigens and/or protein antigens are from at least two distinct arboviruses and/or are from at least *Plasmodium falciparum* and an arbovirus or from *Plasmodium falciparum*.

11. The composition of claim 10, wherein at least one vectored antigen is from CHIKV and at least one protein antigen is from *Plasmodium falciparum*, or wherein at least one vectored antigen is from *Plasmodium falciparum* and at least one protein antigen is from CHIKV.

12. The composition of claim 9, wherein the antigen from *Plasmodium falciparum* is a CS (circumsporozoite) protein, in particular a recombinant CS protein.

13. The composition of claim 8, wherein the antigen from CHIKV comprises structural proteins of the Chikungunya virus, in particular one or several CHIKV structural proteins E1, E2, E3, C and 6K.

14. The composition of claim 1, wherein the mixture of particles encode at least two distinct vectored antigens.

15. The composition of claim 1, wherein the recombinant MV particles have at least one of the following modifications relatively to the wild-type MV:
   deletion of the C protein or of a portion thereof;
   deletion of the V protein or of a portion thereof;
   duplication of the N gene or of a portion thereof.

16. The composition of claim 1, wherein the recombinant MV particles or the modified recombinant Measles viral particles are obtained from a strain selected from the group consisting of Schwarz, Moraten, Edmonston-Zagreb or from the group consisting of CAM-70, TD 97, Leningrad-16, and Shanghai 191 (Ji-191).

17. A method comprising administering the composition of products according to claim 1 to a patient, wherein said vectored antigen is administered and then said protein antigen is administered later to boost the immune response to said vectored antigen.

18. A method of producing modified recombinant MV particles comprising DI particles, comprising the steps of:
   a) rescuing recombinant MV particles encoding at least one antigen (the "vectored antigen") or modified MV particles lacking expression of virulence factors and encoding at least one antigen (the "vectored antigen") from helper cells transfected with cDNA comprising the antigenome of a recombinant MV particle or respectively of a modified recombinant MV particle, wherein said cells express the N, P and L protein of an MV and an RNA polymerase;
   b) recovering the viral particles from the culture of helper cells, or from a co-culture of helper cells with passage cells, i.e. cells suitable for the passage of the recombinant MV or the modified recombinant MV;
   c) infecting passage cells with the recombinant MV or the modified recombinant MV, with an MOI of at least 0.09 and in particular at least 0.1 such as a MOI of 0.09 to 1; and
   d) recovering the recombinant MV particles or the modified recombinant MV particles from the culture of passage cells of c).

19. A viral stock which contains rescued recombinant MV particles or rescued modified recombinant MV particles as defined in claim 1.

* * * * *

SEQUENCE LISTING

```
<160> NUMBER OF SEQ ID NOS: 26

<210> SEQ ID NO 1
<211> LENGTH: 185
<212> TYPE: PRT
<213> ORGANISM: Artificial Sequence
<220> FEATURE:
<223> OTHER INFORMATION: Fragment NS3 protein DENV1

<400> SEQUENCE: 1

Ala Ser Gln Glu Gly Pro Leu Pro Glu Ile Glu Asp Glu Val Phe Arg
1               5                   10                  15

Lys Arg Asn Leu Thr Ile Met Asp Leu His Pro Gly Ser Gly Lys Thr
            20                  25                  30

Arg Arg Tyr Leu Pro Ala Ile Val Arg Glu Ala Ile Lys Arg Lys Leu
        35                  40                  45

Arg Thr Leu Ile Leu Ala Pro Thr Arg Val Val Ala Ser Glu Met Ala
    50                  55                  60

Glu Ala Leu Lys Gly Met Pro Ile Arg Tyr Gln Thr Thr Ala Val Lys
65                  70                  75                  80

Ser Glu His Thr Gly Lys Glu Ile Val Asp Leu Met Cys His Ala Thr
                85                  90                  95

Phe Thr Met Arg Leu Leu Ser Pro Val Arg Val Pro Asn Tyr Asn Met
            100                 105                 110

Ile Ile Met Asp Glu Ala His Phe Thr Asp Pro Ser Ser Ile Ala Ala
        115                 120                 125

Arg Gly Tyr Ile Ser Thr Arg Val Gly Met Gly Glu Ala Ala Ala Ile
    130                 135                 140

Phe Met Thr Ala Thr Pro Pro Gly Ser Val Glu Ala Phe Pro Gln Ser
145                 150                 155                 160

Asn Ala Val Ile Gln Asp Glu Glu Arg Asp Ile Pro Glu Arg Ser Trp
                165                 170                 175

Asn Ser Gly Tyr Glu Trp Ile Thr Asp
            180                 185

<210> SEQ ID NO 2
<211> LENGTH: 134
<212> TYPE: PRT
<213> ORGANISM: Artificial Sequence
<220> FEATURE:
<223> OTHER INFORMATION: Fragment NS3 protein DENV1

<400> SEQUENCE: 2

Glu Asp His Ala His Trp Thr Glu Ala Lys Met Leu Leu Asp Asn Ile
1               5                   10                  15

Asn Thr Pro Glu Gly Ile Ile Pro Ala Leu Phe Glu Pro Glu Arg Glu
```

```
            20                  25                  30

Lys Ser Ala Ala Ile Asp Gly Glu Tyr Arg Leu Arg Gly Glu Ala Arg
        35                  40                  45

Lys Thr Phe Val Glu Leu Met Arg Arg Gly Asp Leu Pro Val Trp Leu
    50                  55                  60

Ser Tyr Lys Val Ala Ser Glu Gly Phe Gln Tyr Ser Asp Arg Arg Trp
65                  70                  75                  80

Cys Phe Asp Gly Glu Arg Asn Asn Gln Val Leu Glu Glu Asn Met Asp
                85                  90                  95

Val Glu Ile Trp Thr Lys Glu Gly Glu Arg Lys Lys Leu Arg Pro Arg
            100                 105                 110

Trp Leu Asp Ala Arg Thr Tyr Ser Asp Pro Leu Ala Leu Arg Glu Phe
        115                 120                 125

Lys Glu Phe Ala Ala Gly
    130

<210> SEQ ID NO 3
<211> LENGTH: 86
<212> TYPE: PRT
<213> ORGANISM: Artificial Sequence
<220> FEATURE:
<223> OTHER INFORMATION: Fragment NS4b protein DENV1

<400> SEQUENCE: 3

Val Ala Val Glu Asn His His His Ala Ala Met Leu Asp Val Asp Leu
1               5                   10                  15

His Pro Ala Ser Ala Trp Thr Leu Tyr Ala Val Ala Thr Thr Ile Ile
            20                  25                  30

Thr Pro Met Met Arg His Thr Ile Glu Asn Thr Thr Ala Asn Ile Ser
        35                  40                  45

Leu Thr Ala Ile Ala Asn Gln Ala Ala Ile Leu Met Gly Leu Asp Lys
    50                  55                  60

Gly Trp Pro Ile Ser Lys Met Asp Ile Gly Val Pro Leu Leu Ala Leu
65                  70                  75                  80

Gly Cys Tyr Ser Gln Val
                85

<210> SEQ ID NO 4
<211> LENGTH: 134
<212> TYPE: PRT
<213> ORGANISM: Artificial Sequence
<220> FEATURE:
<223> OTHER INFORMATION: Fragment NS5 protein DENV1

<400> SEQUENCE: 4

Leu Asp Ile Ile Gly Gln Arg Ile Glu Asn Ile Lys His Glu His Lys
1               5                   10                  15

Ser Thr Trp His Tyr Asp Glu Asp Asn Pro Tyr Lys Thr Trp Ala Tyr
            20                  25                  30

His Gly Ser Tyr Glu Val Lys Pro Ser Gly Ser Ala Ser Ser Met Val
        35                  40                  45

Asn Gly Val Val Lys Leu Leu Thr Lys Pro Trp Asp Val Ile Pro Met
    50                  55                  60

Val Thr Gln Ile Ala Met Thr Asp Thr Thr Pro Phe Gly Gln Gln Arg
65                  70                  75                  80

Val Phe Lys Glu Lys Val Asp Thr Arg Thr Pro Lys Ala Lys Arg Gly
                85                  90                  95
```

```
Thr Ala Gln Ile Met Glu Val Thr Ala Lys Trp Leu Trp Gly Phe Leu
                100                 105                 110
Ser Arg Asn Lys Lys Pro Arg Ile Cys Thr Arg Glu Glu Phe Thr Arg
        115                 120                 125
Lys Val Arg Ser Asn Ala
        130

<210> SEQ ID NO 5
<211> LENGTH: 22
<212> TYPE: DNA
<213> ORGANISM: Artificial Sequence
<220> FEATURE:
<223> OTHER INFORMATION: A2

<400> SEQUENCE: 5
aaagctggga atagaaactt cg                                            22

<210> SEQ ID NO 6
<211> LENGTH: 27
<212> TYPE: DNA
<213> ORGANISM: Artificial Sequence
<220> FEATURE:
<223> OTHER INFORMATION: JM 403

<400> SEQUENCE: 6
cgaagatatt ctggtgtaag tctagta                                       27

<210> SEQ ID NO 7
<211> LENGTH: 22
<212> TYPE: DNA
<213> ORGANISM: Artificial Sequence
<220> FEATURE:
<223> OTHER INFORMATION: JM 402

<400> SEQUENCE: 7
tttatccaga atctcaatcc gg                                            22

<210> SEQ ID NO 8
<211> LENGTH: 23
<212> TYPE: DNA
<213> ORGANISM: Artificial Sequence
<220> FEATURE:
<223> OTHER INFORMATION: Measles genome Forward Primer

<400> SEQUENCE: 8
tcaggcatac ccactagtgt gaa                                           23

<210> SEQ ID NO 9
<211> LENGTH: 23
<212> TYPE: DNA
<213> ORGANISM: Artificial Sequence
<220> FEATURE:
<223> OTHER INFORMATION: Measles genome Reverse Primer

<400> SEQUENCE: 9
tgacagatag cgagtccata acg                                           23

<210> SEQ ID NO 10
<211> LENGTH: 23
<212> TYPE: DNA
<213> ORGANISM: Artificial Sequence
<220> FEATURE:
<223> OTHER INFORMATION: Measles genome TaqMan probe

<400> SEQUENCE: 10
```

```
catcagaatt aagaaaaacg tag                                        23

<210> SEQ ID NO 11
<211> LENGTH: 17
<212> TYPE: DNA
<213> ORGANISM: Artificial Sequence
<220> FEATURE:
<223> OTHER INFORMATION: beta-actin Forward primer

<400> SEQUENCE: 11
accgagcgcg gctacag                                               17

<210> SEQ ID NO 12
<211> LENGTH: 22
<212> TYPE: DNA
<213> ORGANISM: Artificial Sequence
<220> FEATURE:
<223> OTHER INFORMATION: Beta-actin Reverse primer

<400> SEQUENCE: 12
cttaatgtca cgcacgattt cc                                         22

<210> SEQ ID NO 13
<211> LENGTH: 15
<212> TYPE: DNA
<213> ORGANISM: Artificial Sequence
<220> FEATURE:
<223> OTHER INFORMATION: Beta-actin TaqMan probe

<400> SEQUENCE: 13
caccaccacg gccga                                                 15

<210> SEQ ID NO 14
<211> LENGTH: 25
<212> TYPE: DNA
<213> ORGANISM: Artificial Sequence
<220> FEATURE:
<223> OTHER INFORMATION: 504 nt-long DI-RNA Forward primer

<400> SEQUENCE: 14
cggagttcaa ccaattagtc cttaa                                      25

<210> SEQ ID NO 15
<211> LENGTH: 18
<212> TYPE: DNA
<213> ORGANISM: Artificial Sequence
<220> FEATURE:
<223> OTHER INFORMATION: 504 nt-long DI-RNA Reverse primer

<400> SEQUENCE: 15
tgtgccccca gaatttgc                                              18

<210> SEQ ID NO 16
<211> LENGTH: 16
<212> TYPE: DNA
<213> ORGANISM: Artificial Sequence
<220> FEATURE:
<223> OTHER INFORMATION: 504 nt-long DI-RNA TaqMan probe

<400> SEQUENCE: 16
cagggcacta tctagg                                                16

<210> SEQ ID NO 17
<211> LENGTH: 24
<212> TYPE: DNA
<213> ORGANISM: Artificial Sequence
```

```
<220> FEATURE:
<223> OTHER INFORMATION: 1212 nt-long DI-RNA Forward primer

<400> SEQUENCE: 17
ttgcaaataa tgcctaacca ccta                                              24

<210> SEQ ID NO 18
<211> LENGTH: 21
<212> TYPE: DNA
<213> ORGANISM: Artificial Sequence
<220> FEATURE:
<223> OTHER INFORMATION: 1212 nt-long DI-RNA Reverse primer

<400> SEQUENCE: 18
acactgccta cccacgtgac t                                                 21

<210> SEQ ID NO 19
<211> LENGTH: 18
<212> TYPE: DNA
<213> ORGANISM: Artificial Sequence
<220> FEATURE:
<223> OTHER INFORMATION: 1212 nt-long DI-RNA TaqMan probe

<400> SEQUENCE: 19
caggattagg gttccggg                                                     18

<210> SEQ ID NO 20
<211> LENGTH: 25
<212> TYPE: DNA
<213> ORGANISM: Artificial Sequence
<220> FEATURE:
<223> OTHER INFORMATION: 1662 nt-long DI-RNA Forward primer

<400> SEQUENCE: 20
ttaccttaaa aacccactca cgttt                                             25

<210> SEQ ID NO 21
<211> LENGTH: 19
<212> TYPE: DNA
<213> ORGANISM: Artificial Sequence
<220> FEATURE:
<223> OTHER INFORMATION: 1662 nt-long DI-RNA Reverse primer

<400> SEQUENCE: 21
agattgcccc ctgaaatgg                                                    19

<210> SEQ ID NO 22
<211> LENGTH: 16
<212> TYPE: DNA
<213> ORGANISM: Artificial Sequence
<220> FEATURE:
<223> OTHER INFORMATION: 1662 nt-long DI-RNA Taq Man probe

<400> SEQUENCE: 22
aacacaagca agcaca                                                       16

<210> SEQ ID NO 23
<211> LENGTH: 25
<212> TYPE: DNA
<213> ORGANISM: Artificial Sequence
<220> FEATURE:
<223> OTHER INFORMATION: 450 nt-long DI-RNA Forward primer

<400> SEQUENCE: 23
ttatcaactt tttgttcccg gagta                                             25
```

```
<210> SEQ ID NO 24
<211> LENGTH: 21
<212> TYPE: DNA
<213> ORGANISM: Artificial Sequence
<220> FEATURE:
<223> OTHER INFORMATION: 450 nt-long DI-RNA Reverse primer

<400> SEQUENCE: 24
accacctagg gcaggattag g                                              21

<210> SEQ ID NO 25
<211> LENGTH: 23
<212> TYPE: DNA
<213> ORGANISM: Artificial Sequence
<220> FEATURE:
<223> OTHER INFORMATION: 450 nt-long DI-RNA TaqMan Probe

<400> SEQUENCE: 25
agataattgg ttgaactccg gaa                                            23

<210> SEQ ID NO 26
<211> LENGTH: 504
<212> TYPE: DNA
<213> ORGANISM: Artificial Sequence
<220> FEATURE:
<223> OTHER INFORMATION: 504 nt-long DI-RNA of rMV-CHIKV

<400> SEQUENCE: 26
accagacaaa gctgggaata gaaacttcgt attttcaaag ttttctttaa tatattgcaa     60
ataatgccta accacctagg gcaggattag ggttccggag ttcaaccaat tagtccttaa    120
tcagggcact gtatccgact aacttatacc attctttggt ctccttgact gttaccttaa   180
aaacccactc acgtttcaaa cccccgtca taataatctg tttctctgac ttggatagat    240
tcttaacgaa gatattctgg tgtaagtcta gtatcagata gccggacttg agattctgga   300
taaacttatt tatcaactt ttgttcccgg agtaaagaag aatgtgcccc cagaatttgc    360
gggtgatcct agatagtgcc ctgattaagg actaattggt tgaactccgg aaccctaatc   420
ctgccctagg tggttaggca ttatttgcaa tatattaaag aaaactttga aaatacgaag   480
tttctattcc cagctttgtc tggt                                          504
```